（12）United States Patent
Dolezal et al.

(10) Patent No.: US 10,550,144 B2
(45) Date of Patent: Feb. 4, 2020

(54) 6-ARYL-9-GLYCOSYLPURINES AND USE THEREOF

(71) Applicant: UNIVERZITA PALACKEHO V OLOMOUCI, Olomouc (CZ)

(72) Inventors: Karel Dolezal, Hlubocky (CZ); Lucie Plihalova, Olomouc (CZ); Hana Vylicilova, Olomouc (CZ); Marek Zatloukal, Sumperk (CZ); Ondrej Plihal, Olomouc (CZ); Jiri Voller, Brno-Bystrc (CZ); Miroslav Strnad, Olomouc (CZ); Johannes Van Staden, Pietermaritzburg (ZA); Ponnusamy Baskaran, Tamil Nadu (IN); Aloka Kumari, Bihar (IN); Adeyemi Oladapo Aremu, Pietermaritzburg (ZA)

(73) Assignee: UNIVERZITA PALACKEHO V OLOMOUCI, Olomouc (CZ)

( * ) Notice: Subject to any disclaimer, the term of this patent is extended or adjusted under 35 U.S.C. 154(b) by 0 days.

(21) Appl. No.: 15/528,056

(22) PCT Filed: Dec. 2, 2015

(86) PCT No.: PCT/CZ2015/050013
§ 371 (c)(1),
(2) Date: May 18, 2017

(87) PCT Pub. No.: WO2016/091236
PCT Pub. Date: Jun. 16, 2016

(65) Prior Publication Data
US 2017/0326168 A1 Nov. 16, 2017

(30) Foreign Application Priority Data
Dec. 9, 2014 (CZ) .................. PV2014-875

(51) Int. Cl.
| | | |
|---|---|---|
| *A01N 43/04* | (2006.01) | |
| *A61K 31/70* | (2006.01) | |
| *C07H 19/16* | (2006.01) | |
| *A61K 8/60* | (2006.01) | |
| *A61Q 17/04* | (2006.01) | |
| *A61Q 19/08* | (2006.01) | |
| *A61K 31/7076* | (2006.01) | |
| *C07H 19/173* | (2006.01) | |
| *C07H 19/19* | (2006.01) | |
| *A61K 31/7052* | (2006.01) | |
| *A61K 31/7056* | (2006.01) | |
| *A61K 31/706* | (2006.01) | |

(52) U.S. Cl.
CPC ............ *C07H 19/16* (2013.01); *A61K 8/606* (2013.01); *A61K 31/7076* (2013.01); *A61Q 17/04* (2013.01); *A61Q 19/08* (2013.01); *C07H 19/173* (2013.01); *C07H 19/19* (2013.01); *A61K 31/706* (2013.01); *A61K 31/7052* (2013.01); *A61K 31/7056* (2013.01)

(58) Field of Classification Search
None
See application file for complete search history.

(56) References Cited

U.S. PATENT DOCUMENTS

| | | |
|---|---|---|
| 6,294,522 B1 | 9/2001 | Zablocki |
| 2008/0131952 A1 | 6/2008 | Wu et al. |

FOREIGN PATENT DOCUMENTS

| | | |
|---|---|---|
| EP | 2657246 A1 | 10/2013 |
| WO | 2004058791 A2 | 7/2004 |
| WO | 2012084173 A2 | 6/2012 |

OTHER PUBLICATIONS

Kissman et al. JOC (1958), vol. 21, pp. 1053-1055.*
Veldhuyzen et al. J. Am. Chem. Soc. (2001), vol. 123, pp. 11126-11132.*
International Search Report and Written Opinion for corresponding PCT application No. PCT/CZ2015/050013, dated Mar. 3, 2016.

* cited by examiner

*Primary Examiner* — Patrick T Lewis
(74) *Attorney, Agent, or Firm* — Notaro, Michalos & Zaccaria P.C.

(57) ABSTRACT

6-aryl-9-glycosidpurines of general formula I

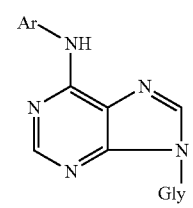

and pharmaceutically acceptable salts thereof with alkali metals, ammonia, amines, or addition salts with acids, wherein Gly represents β-D-arabinofuranosyl or β-D-2'-deoxyribofuranosyl, Ar represents benzyl or furfuryl, each of which can be unsubstituted or substituted by one or more, preferably one to three, substituents selected from the group comprising hydroxyl, alkyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy, for use for regulation, in particular inhibition, of aging in plants in vivo or plant cells in vitro, and for regulation of growth and development of plants in vivo, plant tissues, plant organs and plant cells in vitro.

5 Claims, 2 Drawing Sheets

6-ARYL-9-GLYCOSYLPURINES AND USE THEREOF

FIELD OF ART

The invention relates to 6-(benzylamino/furfurylamino)-9-β-D-arabinofuranosylpurine or -β-D-2'-deoxyribofuranosylpurine derivatives which regulate the growth, development and aging of plants in vivo and plant cells in vitro (e.g., in tissue cultures or production cultures).

BACKGROUND ART

Substituted adenine derivatives are known as phytohormones. The range of their properties is rather broad, especially known is their anti-tumor and pro-apoptotic activity, i.e., activities relating to inhibition of tumor cell growth. Several glycosylated derivatives were prepared, in particular ribosylated derivatives. An arabinosylated derivative prepared so far was 6-benzylamino-9-arabinosylpurine which was published as a compound participating in inhibition of replication of tobacco mosaic virus in extirpated leaves *Nicotiana glutinosa* (Barai et al. Vestsi Akademii Nauk Belarusi 1: 18-22, 1992). 6-chloropurine arabinoside was prepared from 6-chloropurine riboside and its antiviral activity was explored (Maruyama et al. Chem. Pharm. Bull. 44: 2331-2334, 1996). Several methylated derivatives of 6-(benzylamino)-9-β-D-arabinofuranosylpurine were prepared for antiviral activity testing, and their activity in killing Vaccinia virus and Herpes simplex virus was tested. No effect was observed for benzylamino derivative, neither for 2-methylbenzyl, 3-methylbenzyl, 2,3-dimethylbenzyl, 2,6-dimethylbenzyl, 3,4-dimethylbenzyl derivatives. A low activity against Vaccinia virus, strain IHD, was observed for 2,4-dimethylbenzyl and 2,5-dimethylbenzyl substituents (Masakatsu et al. Chem. Pharm. Bull. 25: 2482-2489, 1977). Some N6-substituted derivatives of adenine arabinoside were prepared as selective inhibitors of varicella-zoster virus, the substituents were 6-methylamino, 6-dimethylamino-, 6-ethylamino-, 6-N-ethylmethylamino-, NN-diethylamino-, 6-n-propylamino-, 6-isopropylamino-, 6-n-hexylamino-, 6-cyclohexylamino-, 6-anilino (Koszalka et al. Antimicrob. Agents Chemother. 35: 1437-1443, 1991).

The object of the present invention are glycosylated derivatives of adenine with antisenescent and development-regulating properties which show extremely low or no toxicity and high activity in aging, cell division and differentiation processes.

DISCLOSURE OF THE INVENTION

Object of the invention is use of 6-aryl-9-glycosylpurines of general formula I

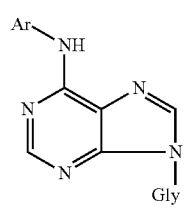

and pharmaceutically acceptable salts thereof with alkali metals, ammonia, amines, or addition salts with acids, wherein Gly represents β-D-arabinofuranosyl or β-D-2'-deoxyribofuranosyl, Ar represents benzyl or furfuryl, each of which can be unsubstituted or substituted by one or more, preferably one to three, substituents selected from the group comprising hydroxyl, alkyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy, for regulation, in particular inhibition, of aging in plants in vivo or plant cells in vitro, and for regulation of growth and development of plants in vivo, plant tissues, plant organs and plant cells in vitro.

The regulation of development of plants and plant cells in one preferred embodiment represents controlling, preferably inhibiting, necrosis in plants and plant organs, such as leaves and flowers.

Another object of the invention is a method for regulation, in particular inhibition, of aging in plants in vivo or plant cells in vitro, and for regulation of growth and development of plants in vivo, plant tissues, plant organs and plant cells in vitro, in which at least one compound of general formula I is applied to the plant, plant tissues, plant organs or plant cells.

If not stated otherwise, then:

alkyl represents a linear or branched C1-C6, preferably C1-C4, alkyl chain, acyl represents an acyl group having 2 to 6 carbon atoms, halogen represents a halogen atom selected from the group consisting of fluorine, bromine, chlorine and iodine atom, sulfo represents —SO$_3$R$_c$, wherein R$_c$ represents hydrogen atom, linear or branched alkyl, alkenyl or alkynyl group containing 1 to 6 carbon atoms, sulfoamido represents —NHSO$_3$R$_d$, wherein R$_d$ represents hydrogen atom, linear or branched alkyl group containing 1 to 6 carbon atoms.

Particularly preferred compounds of the invention are the compounds of formula I selected from the group consisting of: 6-furfurylamino-9-β-D-arabinofuranosylpurine, 6-(3-methylfurfurylamino)-9-β-D-arabinofuranosylpurine, 6-(4-methylfurfurylamino)-9-β-D-arabinofuranosylpurine, 6-(5-methylfurfurylamino)-9-β-D-arabinofuranosylpurine, 6-(3-fluorofurfurylamino)-9-β-D-arabinofuranosylpurine, 6-(4-fluorofurfurylamino)-9-β-D-arabinofuranosylpurine, 6-(5-fluorofurfurylamino)-9-β-D-arabinofuranosylpurine, 6-(3-chlorofurfurylamino)-9-β-D-arabinofuranosylpurine, 6-(4-chlorofurfurylamino)-9-β-D-arabinofuranosylpurine, 6-(5-chlorofurfurylamino)-9-β-D-arabinofuranosylpurine, 6-(3-bromofurfurylamino)-9-β-D-arabinofuranosylpurine, 6-(4-bromofurfurylamino)-9-β-D-arabinofuranosylpurine, 6-(5-bromofurfurylamino)-9-β-D-arabinofuranosylpurine, 6-(3-hydroxyfurfurylamino)-9-β-D-arabinofuranosylpurine, 6-(4-hydroxyfurfurylamino)-9-β-D-arabinofuranosylpurine, 6-(5-hydroxyfurfurylamino)-9-β-D-arabinofuranosylpurine, 6-(3-methoxyfurfurylamino)-9-β-D-arabinofuranosylpurine, 6-(4-methoxyfurfurylamino)-9-β-D-arabinofuranosylpurine, 6-(5-methoxyfurfurylamino)-9-β-D-arabinofuranosylpurine, 6-(2-aminofurfurylamino)-9-β-D-arabinofuranosylpurine, 6-(3-aminofurfurylamino)-9-β-D-arabinofuranosylpurine, 6-(4-aminofurfurylamino)-9-β-D-arabinofuranosylpurine, 6-(3,4-dihydroxyfurfurylamino)-9-β-D-arabinofuranosylpurine, 6-(3,5-dihydroxyfurfurylamino)-9-β-D-arabinofuranosylpurine, 6-(3,4-dihydroxyfurfurylamino)-9-β-D-arabinofuranosylpurine, dihydroxyfurfurylamino)-9-β-D-arabinofuranosylpurine, 6-(2,5-dihydroxyfurfurylamino)-9-β-D-arabinofuranosylpurine, 6-(2,6-dihydroxyfurfurylamino)-9-β-D-arabinofuranosylpurine, dimethoxyfurfurylamino)-9-β-D-arabinofuranosylpurine, 6-(3,4-dimethoxyfurfurylamino)-9-β-D-arabinofuranosylpurine, 6-(3,5-dimethoxyfurfurylamino)-9-β-D-arabinofuranosylpurine, 6-(2,3-dimethoxyfurfurylamino)-9-β-D-arabinofuranosylpurine, 6-(2,4-dimethoxyfurfurylamino)-9-β-D-arabinofuranosylpurine, 6-(2,5-dimethoxyfurfurylamino)-9-β-D-arabinofuranosylpurine, dimethoxyfurfurylamino)-9-β-D-arabinofuranosylpurine, 6-(2-hydroxy-3-methoxyfurfurylamino)-9-β-D-arabinofuranosylpurine, 6-(2-hydroxy-4-methoxyfurfurylamino)-9-β-D-arabinofuranosylpurine, 6-(2-hydroxy-5-methoxyfurfurylamino)-9-β-D-arabinofuranosylpurine, 6-(2-hydroxy-6-methoxyfurfurylamino)-9-β-D-arabinofuranosylpurine, 6-(3-hydroxy-2-methoxyfurfurylamino)-9-β-D-arabinofuranosylpurine, 6-(3-hydroxy-4-methoxyfurfurylamino)-9-β-D-arabinofuranosylpurine, 6-(3-hydroxy-5-methoxyfurfurylamino)-9-β-D-arabinofuranosylpurine, 6-(3-hydroxy-6-methoxyfurfurylamino)-9-β-D-arabinofuranosylpurine, 6-(4-hydroxy-2-methoxyfurfurylamino)-9-β-D-arabinofuranosylpurine, 6-(4-hydroxy-3-methoxyfurfurylamino)-9-β-D-arabinofuranosylpurine, 6-(4-hydroxy-5-methoxyfurfurylamino)-9-β-D-arabinofuranosylpurine, 6-(4-hydroxy-6-methoxyfurfurylamino)-9-β-D-arabinofuranosylpurine, 6-(2-fluorobenzylamino)-9-β-D-arabinofuranosylpurine, 6-(3-fluorobenzylamino)-9-β-D-arabinofuranosylpurine, 6-(4-fluorobenzylamino)-9-β-D-arabinofuranosylpurine, 6-(2-bromobenzylamino)-9-β-D-arabinofuranosylpurine, 6-(3-bromobenzylamino)-9-β-D-arabinofuranosylpurine, 6-(4-bromobenzylamino)-9-β-D-arabinofuranosylpurine, 6-(2-iodobenzylamino)-9-β-D-arabinofuranosylpurine, 6-(3-iodobenzylamino)-9-β-D-arabinofuranosylpurine, 6-(4-iodobenzylamino)-9-β-D-arabinofuranosylpurine, 6-(2-chlorobenzylamino)-9-β-D-arabinofuranosylpurine, 6-(2-chlorobenzylamino)-9-β-D-arabinofuranosylpurine, 6-(3-chlorobenzylamino)-9-β-D-arabinofuranosylpurine, 6-(4-chlorobenzylamino)-9-β-D-arabinofuranosylpurine, 6-(2-methoxybenzylamino)-9-β-D-arabinofuranosylpurine, 6-(3-methoxybenzylamino)-9-β-D-arabinofuranosylpurine, 6-(4-methoxybenzylamino)-9-β-D-arabinofuranosylpurine, 6-(2-hydroxybenzylamino)-9-β-D-arabinofuranosylpurine, 6-(3-hydroxybenzylamino)-9-β-D-arabinofuranosylpurine, 6-(4-hydroxybenzylamino)-9-β-D-arabinofuranosylpurine, 6-(4-hexylbenzylamino)-9-β-D-arabinofuranosylpurine, 6-(2-fluoro-6-(trifluoromethyl)benzylamino)-9-β-D-arabinofuranosylpurine, 6-(3-chloro-2,6-difluorobenzylamino)-9-β-D-arabinofuranosylpurine, 6-(3-(trifluoromethylthio)benzylamino)-9-β-D-arabinofuranosylpurine, 6-(2-chloro-3,6-difluorobenzylamino)-9-β-D-arabinofuranosylpurine, 6-(4-(trifluoromethylthio)benzylamino)-9-β-D-arabinofuranosylpurine, 6-(3-fluoro-5-(trifluoromethyl)benzylamino)-9-β-D-arabinofuranosylpurine, 6-(2-chloro-4-fluorobenzylamino)-9-β-D-arabinofuranosylpurine, 6-(2-(trifluoromethoxy)benzylamino)-9-β-D-arabinofuranosylpurine, 6-(3-(trifluoromethyl)benzylamino)-9-β-D-arabinofuranosylpurine, 6-(2-(trifluoromethyl)benzylamino)-9-β-D-arabinofuranosylpurine, 6-(4-(trifluoromethyl)benzylamino)-9-β-D-arabinofuranosylpurine, 6-(4-chloro-3-(trifluoromethyl)benzylamino)-9-β-D-arabinofuranosylpurine, 6-(4-fluoro-3-(trifluoromethyl)benzylamino)-9-β-D-arabinofuranosylpurine, 6-(3,5-bis(trifluoromethyl)benzylamino)-9-β-D-arabinofuranosylpurine, 6-(3-(trifluoromethoxy)benzylamino)-9-β-D-arabinofuranosylpurine, 6-(4-(trifluoromethoxy)benzylamino)-9-β-D-arabinofuranosylpurine, 6-(4-(trifluoromethyl)benzylamino)-9-β-D-arabinofuranosylpurine, 6-(2-aminobenzylamino)-9-β-D-arabinofuranosylpurine, 6-(3-aminobenzylamino)-9-β-D-arabinofuranosylpurine, 6-(4-aminobenzylamino)-9-β-D-arabinofuranosylpurine, 6-(4-diethylaminobenzylamino)-9-β-D-arabinofuranosylpurine, 6-(3,4-dihydroxybenzylamino)-9-β-D-arabinofuranosylpurine, 6-(3,5-dihydroxybenzylamino)-9-β-D-arabinofuranosylpurine, 6-(3,4-dihydroxybenzylamino)-9-β-D-arabinofuranosylpurine, 6-(2,4-dihydroxybenzylamino)-9-β-D-arabinofuranosylpurine, 6-(2,5-dihydroxybenzylamino)-9-β-D-arabinofuranosylpurine, 6-(2,6-dihydroxybenzylamino)-9-β-D-arabinofuranosylpurine, 6-(3,4-dimethoxybenzylamino)-9-β-D-arabinofuranosylpurine, 6-(3,4-dimethoxybenzylamino)-9-β-D-arabinofuranosylpurine, 6-(3,5-dimethoxybenzylamino)-9-β-D-arabinofuranosylpurine, 6-(2,3-dimethoxybenzylamino)-9-β-D-arabinofuranosylpurine, 6-(2,4-dimethoxybenzylamino)-9-β-D-arabinofuranosylpurine, 6-(2,5-dimethoxybenzylamino)-9-β-D-arabinofuranosylpurine, 6-(2,6-dimethoxybenzylamino)-9-β-D-arabinofuranosylpurine, 6-(2-hydroxy-3-methoxybenzylamino)-9-β-D-arabinofuranosylpurine, 6-(2-hydroxy-4-methoxybenzylamino)-9-β-D-arabinofuranosylpurine, 6-(2-hydroxy-5-methoxybenzylamino)-9-β-D-arabinofuranosylpurine, 6-(2-hydroxy-6-methoxybenzylamino)-9-β-D-arabinofuranosylpurine, 6-(3-hydroxy-2-methoxybenzylamino)-9-β-D-arabinofuranosylpurine, 6-(3-hydroxy-4-methoxybenzylamino)-9-β-D-arabinofuranosylpurine, 6-(3-hydroxy-5-methoxybenzylamino)-9-β-D-arabinofuranosylpurine, 6-(3-hydroxy-6-methoxybenzylamino)-9-β-D-arabinofuranosylpurine, 6-(4-hydroxy-2-methoxybenzylamino)-9-β-D-arabinofuranosylpurine, 6-(4-hydroxy-3-methoxybenzylamino)-9-β-D-arabinofuranosylpurine, 6-(4-hydroxy-5-methoxybenzylamino)-9-β-D-arabinofuranosylpurine, 6-(4-hydroxy-6-methoxybenzylamino)-9-β-D-arabinofuranosylpurine, 6-(2,3,4-trimethoxybenzylamino)-9-β-D-arabinofuranosylpurine, 6-(2,4,5-trimethoxybenzylamino)-9-β-D-arabinofuranosylpurine, 6-(2,4,6-trimethoxybenzylamino)-9-β-D-arabinofuranosylpurine, 6-(3,4,5-trimethoxybenzylamino)-9-β-D-arabinofuranosylpurine, 6-(2-hydroxy-3,4,5-trimethoxybenzylamino)-9-β-D-arabinofuranosylpurine, 6-(2-hydroxy-3,4,6-trimethoxybenzylamino)-9-β-D-arabinofuranosylpurine, 6-(2-hydroxy-4,5,6-trimethoxybenzylamino)-9-β-D-arabinofuranosylpurine, 6-(2,4,6-trimethoxybenzylamino)-9-β-D-arabinofuranosylpurine, 6-(2,3,4-trihydroxybenzylamino)-9-β-D-arabinofuranosylpurine, 6-(2,4,6-trihydroxybenzylamino)-9-β-D-arabinofuranosylpurine, 6-(2,3,4-trihydroxybenzylamino)-9-β-D-arabinofuranosylpurine, 6-(3,4,5-trihydroxybenzylamino)-9-β-D-arabinofuranosylpurine, 6-(2,4,6-trihydroxybenzylamino)-9-β-D-arabinofuranosylpurine, 6-(2-hydroxy-3-chlorobenzylamino)-9-β-D-arabinofuranosylpurine, 6-(2-hydroxy-4-chlorobenzylamino)-9-β-D-arabinofuranosylpurine, 6-(2-hydroxy-5-chlorobenzylamino)-9-β-D-arabinofuranosylpurine, 6-(2-hydroxy-6-chlorobenzylamino)-9-β-D-arabinofuranosylpurine, 6-(2-hydroxy-3-iodobenzylamino)-9-β-D-arabinofuranosylpurine, 6-(2-hydroxy-4-iodobenzylamino)-9-β-D-arabinofuranosylpurine, 6-(2-hydroxy-5-iodobenzylamino)-9-β-D- arabinofuranosylpurine, 6-(2-hydroxy-6-iodobenzylamino)-9-β-D-arabinofuranosylpurine, 6-(2-hydroxy-3-bromobenzylamino)-9-β-D-arabinofuranosylpurine, 6-(2-hydroxy-4-bromobenzylamino)-9-β-D-arabinofuranosylpurine, 6-(2-hydroxy-5-bromobenzylamino)-9-β-D-arabinofuranosylpurine, 6-(2-hydroxy-6-bromobenzylamino)-9-β-D-arabinofuranosylpurine, 6-(2-hydroxy-3-fluorobenzylamino)-9-β-D-arabinofuranosylpurine, 6-(2-hydroxy-4-fluorobenzylamino)-9-β-D-arabinofuranosylpurine, 6-(2-hydroxy-5-fluorobenzylamino)-9-β-D-arabinofuranosylpurine, 6-(3-methylfurfurylamino)-9-β-D-2'-deoxyribofuranosylpurine, 6-(4-methylfurfurylamino)-9-β-D-2'-deoxyribofuranosylpurine, 6-(5-methylfurfurylamino)-9-β-D-2'-deoxyribofuranosylpurine, 6-(3-fluorofurfurylamino)-9-β-D-2'-deoxyribofuranosylpurine, 6-(4-fluorofurfurylamino)-9-β-D-2'-deoxyribofuranosylpurine, 6-(5-fluorofurfurylamino)-9-β-D-2'-deoxyribofuranosylpurine, 6-(3-chlorofurfurylamino)-9-β-D-2'-deoxyribofuranosylpurine, 6-(4-chlorofurfurylamino)-9-β-D-2'-deoxyribofuranosylpurine, 6-(5-chlorofurfurylamino)-9-β-D-2'-deoxyribofuranosylpurine, 6-(3-bromo-furfurylamino)-9-β-D-2'-deoxyribofuranosylpurine, 6-(4-bromofurfurylamino)-9-β-D-2'-deoxyribofuranosylpurine, 6-(5-bromofurfurylamino)-9-β-D-2'-deoxyribofuranosylpurine, 6-(3-hydroxyfurfurylamino)-9-β-D-2'-deoxyribofuranosylpurine, 6-(4-hydroxyfurfurylamino)-9-β-D-2'-deoxyribofuranosylpurine, 6-(5-hydroxyfurfurylamino)-9-β-D-2'-deoxyribofuranosylpurine, 6-(3-methoxyfurfurylamino)-9-β-D-2'-deoxyribofuranosylpurine, 6-(4-methoxyfurfurylamino)-9-β-D-2'-deoxyribofuranosylpurine, 6-(5-methoxyfurfurylamino)-9-β-D-2'-deoxyribofuranosylpurine, 6-(2-aminofurfurylamino)-9-β-D-2'-deoxyribofuranosylpurine, 6-(3-aminofurfurylamino)-9-β-D-2'-deoxyribofuranosylpurine, 6-(4-aminofurfurylamino)-9-β-D-2'-deoxyribofuranosylpurine, 6-(3,4-dihydroxyfurfurylamino)-9-β-D-2'-deoxyribofuranosylpurine, 6-(3,5-dihydroxyfurfurylamino)-9-β-D-2'-deoxyribofuranosylpurine, 6-(3,4-dihydroxyfurfurylamino)-9-β-D-2'-deoxyribofuranosylpurine, 6-(2,4-dihydroxyfurfurylamino)-9-β-D-2'-deoxyribofuranosylpurine, 6-(2,5-dihydroxyfurfurylamino)-9-β-D-2'-deoxyribofuranosylpurine, 6-(2,6-dihydroxyfurfurylamino)-9-β-D-2'-deoxyribofuranosylpurine, 6-(3,4-dimethoxyfurfurylamino)-9-β-D-2'-deoxyribofuranosylpurine, 6-(3,4-dimethoxyfurfurylamino)-9-β-D-2'-deoxyribofuranosylpurine, 6-(3,5-dimethoxyfurfurylamino)-9-β-D-2'-deoxyribofuranosylpurine, 6-(2,3-dimethoxyfurfurylamino)-9-β-D-2'-deoxyribofuranosylpurine, 6-(2,4-dimethoxyfurfurylamino)-9-β-D-2'-deoxyribofuranosylpurine, 6-(2,5-dimethoxyfurfurylamino)-9-β-D-2'-deoxyribofuranosylpurine, 6-(2,6-dimethoxyfurfurylamino)-9-β-D-2'-deoxyribofuranosylpurine, 6-(2-hydroxy-3-methoxyfurfurylamino)-9-β-D-2'-deoxyribofuranosylpurine, 6-(2-hydroxy-4-methoxyfurfurylamino)-9-β-D-2'-deoxyribofuranosylpurine, 6-(2-hydroxy-5-methoxyfurfurylamino)-9-β-D-2'-deoxyribofuranosylpurine, 6-(2-hydroxy-6-methoxyfurfurylamino)-9-β-D-2'-deoxyribofuranosylpurine, 6-(3-hydroxy-2-methoxyfurfurylamino)-9-β-D-2'-deoxyribofuranosylpurine, 6-(3-hydroxy-4-methoxyfurfurylamino)-9-β-D-2'-deoxyribofuranosylpurine, 6-(3-hydroxy-5-methoxyfurfurylamino)-9-β-D-2'-deoxyribofuranosylpurine, 6-(3-hydroxy-6-methoxyfurfurylamino)-9-β-D-2'-deoxyribofuranosylpurine, 6-(4-hydroxy-2-methoxyfurfurylamino)-9-β-D-2'-deoxyribofuranosylpurine, 6-(4-hydroxy-3-methoxyfurfurylamino)-9-β-D-2'-deoxyribofuranosylpurine, 6-(4-hydroxy-5-methoxyfurfurylamino)-9-β-D-2'-deoxyribofuranosylpurine, 6-(4-hydroxy-6-methoxyfurfurylamino)-9-β-D-2'-deoxyribofuranosylpurine, 6-(2-fluorobenzylamino)-9-β-D-2'-deoxyribofuranosylpurine, 6-(3-fluorobenzylamino)-9-β-D-2'-deoxyribofuranosylpurine, 6-(4-fluorobenzylamino)-9-β-D-2'-deoxyribofuranosylpurine, 6-(2-bromobenzylamino)-9-β-D-2'-deoxyribofuranosylpurine, 6-(3-bromobenzylamino)-9-β-D-2'-deoxyribofuranosylpurine, 6-(4-bromobenzylamino)-9-β-D-2'-deoxyribofuranosylpurine, 6-(2-iodobenzylamino)-9-β-D-2'-deoxyribofuranosylpurine, 6-(3-iodobenzylamino)-9-β-D-2'-deoxyribofuranosylpurine, 6-(4-iodobenzylamino)-9-β-D-2'-deoxyribofuranosylpurine, 6-(2-chlorobenzylamino)-9-β-D-2'-deoxyribofuranosylpurine, 6-(2-chlorobenzylamino)-9-β-D-2'-deoxyribofuranosylpurine, 6-(3-chlorobenzylamino)-9-β-D-2'-deoxyribofuranosylpurine, 6-(4-chlorobenzylamino)-9-β-D-2'-deoxyribofuranosylpurine, 6-(2-aminobenzylamino)-9-β-D-2'-deoxyribofuranosylpurine, 6-(3-aminobenzylamino)-9-β-D-2'-deoxyribofuranosylpurine, 6-(4-aminobenzylamino)-9-β-D-2'-deoxyribofuranosylpurine, 6-(2-methoxybenzylamino)-9-β-D-2'-deoxyribofuranosylpurine, 6-(3-methoxybenzylamino)-9-β-D-2'-deoxyribofuranosylpurine, 6-(4-methoxybenzylamino)-9-β-D-2'-deoxyribofuranosylpurine, 6-(2-hydroxybenzylamino)-9-β-D-2'-deoxyribofuranosylpurine, 6-(3-hydroxybenzylamino)-9-β-D-2'-deoxyribofuranosylpurine, 6-(4-hydroxybenzylamino)-9-β-D-2'-deoxyribofuranosylpurine, 6-(3,4-dihydroxybenzylamino)-9-β-D-2'-deoxyribofuranosylpurine, 6-(3,5-dihydroxybenzylamino)-9-β-D-2'-deoxyribofuranosylpurine, 6-(3,4-dihydroxybenzylamino)-9-β-D-2'-deoxyribofuranosylpurine, 6-(2,4-dihydroxybenzylamino)-9-β-D-2'-deoxyribofuranosylpurine, 6-(2,5-dihydroxybenzylamino)-9-β-D-2'-deoxyribofuranosylpurine, 6-(2,6-dihydroxybenzylamino)-9-β-D-2'-deoxyribofuranosylpurine, 6-(3,4-dimethoxybenzylamino)-9-β-D-2'-deoxyribofuranosylpurine, 6-(3,4-dimethoxybenzylamino)-9-β-D-2'-deoxyribofuranosylpurine, 6-(3,5-dimethoxybenzylamino)-9-β-D-2'-deoxyribofuranosylpurine, 6-(2,3-dimethoxybenzylamino)-9-β-D-2'-deoxyribofuranosylpurine, 6-(2,4-dimethoxybenzylamino)-9-β-D-2'-deoxyribofuranosylpurine, 6-(2,5-dimethoxybenzylamino)-9-β-D-2'-deoxyribofuranosylpurine, 6-(2,6-dimethoxybenzylamino)-9-β-D-2'-deoxyribofuranosylpurine, 6-(2-hydroxy-3-methoxybenzylamino)-9-β-D-2'-deoxyribofuranosylpurine, 6-(2-hydroxy-4-methoxybenzylamino)-9-β-D-2'-deoxyribofuranosylpurine, 6-(2-hydroxy-5-methoxybenzylamino)-9-β-D-2'-deoxyribofuranosylpurine, 6-(2-hydroxy-6-methoxybenzylamino)-9-β-D-2'-deoxyribofuranosylpurine, 6-(3-hydroxy-2-methoxybenzylamino)-9-β-D-2'-deoxyribofuranosylpurine, 6-(3-hydroxy-4-methoxybenzylamino)-9-β-D-2'-deoxyribofuranosylpurine, 6-(3-hydroxy-5-methoxybenzylamino)-9-β-D-2'-deoxyribofuranosylpurine, 6-(3-hydroxy-6-methoxybenzylamino)-9-β-D-2'-deoxyribofuranosylpurine, 6-(4-hydroxy-2-methoxybenzylamino)-9-β-D-2'-deoxyribofuranosylpurine, 6-(4-hydroxy-3-methoxybenzylamino)-9-β-D-2'-deoxyribofuranosylpurine, 6-(4-hydroxy-5-methoxybenzylamino)-9-β-D-2'-deoxyribofuranosylpurine, 6-(4-hydroxy-6-methoxybenzylamino)-9-β-D-2'-deoxyribofuranosylpurine.

Object of the invention are also 6-aryl-9-glycosidpurines of general formula Ia

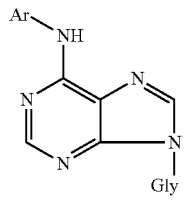

Ia and pharmaceutically acceptable salts thereof with alkali metals, ammonia, amines, or addition salts with acids, wherein
Gly represents β-D-arabinofuranosyl or β-D-2'-deoxyribofuranosyl,
Ar represents benzyl or furfuryl, each of which is substituted by one or more, preferably one to three, substituents selected from the group comprising hydroxyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy, or Ar is unsubstituted furfuryl, whereas, if Gly is β-D-arabinofuranosyl, Ar is not methyl-substituted benzyl.

Object of the invention are further compositions for regulation, in particular inhibition, of aging in plants in vivo or plant cells in vitro, and for regulation of growth and development of plants in vivo, plant tissues, plant organs and plant cells in vitro, containing at least one 6-aryl-9-glycosidpurine of general formula Ia.

The invention further encompasses tissue culture and/or growth-regulating compositions containing as an active ingredient at least one compound of general formula Ia. Tissue culture compositions are especially suitable for use in biotechnologies, in particular in tissue cultures for micropropagation of plants. Growth-regulating compositions are destined for use in agriculture, in particular for increasing the yield and quality of agricultural products.

Preparations

The preparations comprising the compounds of general formula I (active ingredients) and, where appropriate, one or more solid or liquid excipients, are prepared in a manner known per se e.g. by mixing and/or grinding the active ingredients with excipients, e.g. solvents or solid carriers. In addition, surface-active compounds (surfactants) may also be used in the preparations.

Depending on the nature of the compound to be formulated, suitable surface-active compounds are non-ionic, cationic and/or anionic surfactants and surfactant mixtures having good emulsifying, dispersing and wetting properties.

Examples of suitable anionic, non-ionic and cationic surfactants are listed, for example, in WO 97/34485.

Also suitable in the preparation of the compositions containing compounds according to the invention are the surfactants conventionally used in formulation technology, which are described, inter alia, in "McCutcheon's Detergents and Emulsifiers Annual" MC Publishing Corp., Ridgewood N.J., 1981; Stache, H., "Tensid-Taschenbuch", Carl Hanser Verlag, Munich, 1981; and M. and J. Ash, "Encyclopedia of Surfactants", Vol. 1-3, Chemical Publishing Co., New York, 1980-81.

The formulation of the preparation containing compounds usually contains from 0.1 to 95% active ingredient by weight, from 5 to 99.9% by weight of solid or liquid adjuvants or pharmaceutical carriers, depending on the application method, and from 0.1 to 25% by weight of a surfactant.

Whereas commercial products are usually formulated as concentrates, the end user will normally employ dilute formulations. The compositions may also comprise further ingredients, such as stabilisers, e.g. vegetable oils or epoxidised vegetable oils (epoxidised coconut 0; 1, rapeseed oil or soybean oil), antifoams, e.g. silicone oil, preservatives, stabilizers, wetting agents or emulsifiers, viscosity factors, binders, tackifiers, and also fertilisers or other active ingredients. Preferred formulations have especially the following compositions: (%=percent by weight)

Emulsifiable Concentrates:
active ingredient mixture: 1 to 90%, preferably 5 to 20%
surfactant: 1 to 30%, preferably 10 to 20%
liquid carrier: 5 to 94%, preferably 70 to 85%
Dusts:
active ingredient mixture: 0.1 to 10%, preferably 0.1 to 5%
solid carrier: 99.9 to 90%, preferably 99.9 to 95%
Suspension Concentrates:
active ingredient mixture: 5 to 75%, preferably 10 to 50%
water: 94 to 24%, preferably 88 to 30%
surfactant: 1 to 40%, preferably 2 to 30%
Wettable Powders:
active ingredient mixture: 0.5 to 90%, preferably 1 to 80%
surfactant: 0.5 to 20%, preferably 1 to 15%
solid carrier: 5 to 95%, preferably 15 to 90%
Granules:
active ingredient mixture: 0.1 to 30%, preferably 0.1 to 15%
solid carrier: 99.9 to 70%, preferably 99.9 to 85%

The compositions may also comprise further ingredients, such as stabilisers, e.g. vegetable oils or epoxidised vegetable oils (epoxidised coconut oil, rapeseed oil or soybean oil), anti-foams, e.g. silicone oil, preservatives, viscosity regulators, binders, tackifiers, and also fertilisers or other active ingredients. For the use of the compounds of general formula I, or of compositions comprising them, in the protection of crop plants against the damaging effects of growth regulators, various methods and techniques come into consideration, such as, for example, the following:

i) Seed Dressing
a) Dressing of the seeds with a wettable powder formulation of a compound of the general formula I by shaking in a vessel until uniformly distributed over the seed surface (dry dressing). In that procedure approximately from 1 to 500 g of compound of the general formula I (4 g to 2 kg of wettable powder) are used per 100 kg of seed.
b) Dressing of the seeds with an emulsifiable concentrate of a compound of formula I according to method a) (wet dressing).

c) Dressing by immersing the seeds for from 1 to 72 hours in a liquor comprising from 100 to 1000 ppm of a compound of general formula I and preferably subsequently drying the seeds (immersion dressing).

Dressing the seeds or treating the germinated seedlings are naturally the preferred methods of application, because treatment with the active ingredients is directed entirely at the target crop. Generally from 1 to 1000 g of antidote, preferably from 5 to 250 g of antidote, are used per 100 kg of seed, but depending on the methodology, which also enables the addition of other active ingredients or micronutrients, the concentration limits indicated can be varied up or down (repeat dressing).

ii) Application as a Tank Mixture

A liquid formulation is used in the amount of 0.005 to 5.0 kg per hectare. Such tank mixtures are applied before or after sowing.

iii) Application to the Seed Furrow

The compounds of formula I are introduced into the open, sown seed furrow in the form of an emulsifiable concentrate, wettable powder or granules. Once the seed furrow has been covered over, the growth regulator is applied in the usual manner in the pre-emergence process.

iv) Controlled Release of Active Ingredient

The compounds of formula I are applied in solution to mineral granule carriers or polymerised granules (urea/formaldehyde) and dried. If desired, it is also possible to apply a coating that allows the active ingredient to be released in metered amounts over a specific period of time (coated granules).

The invention is further illustrated by the following examples which should not be construed as further limiting.

EXAMPLES OF CARRYING OUT THE INVENTION

Figure 1:
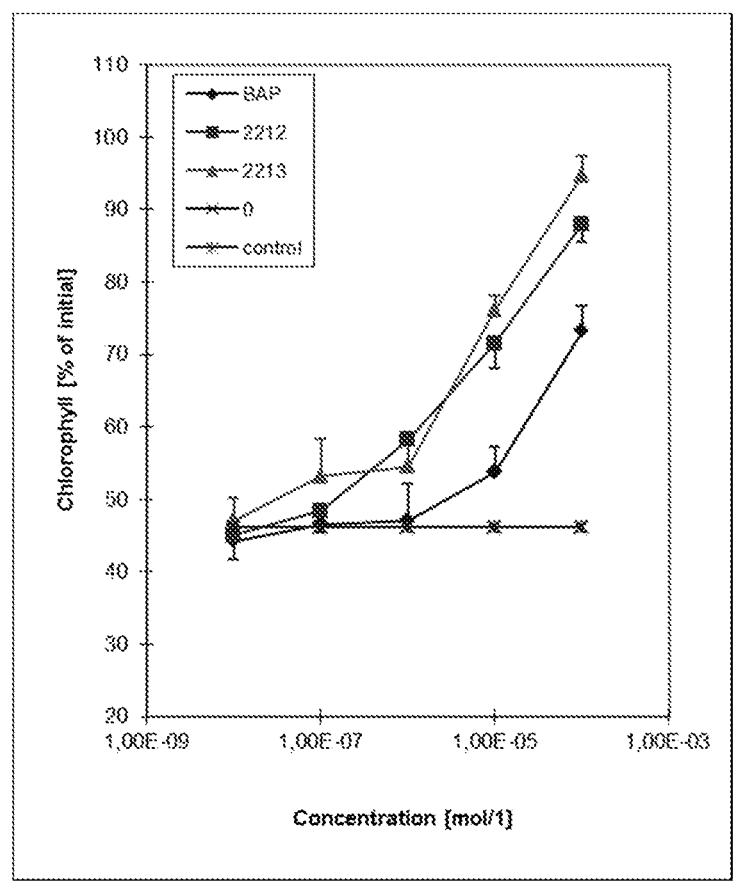
FIG. 1: Effect of 6-furfurylamino-9-β-D-arabinofuranosylpurine (2212) and 3-fluorobenzylamino-9-β-D-arabinofuranosylpurine (2213) on the retention of chlorophyll in extirpated wheat leaf segments (Example 15).
Figure 2:
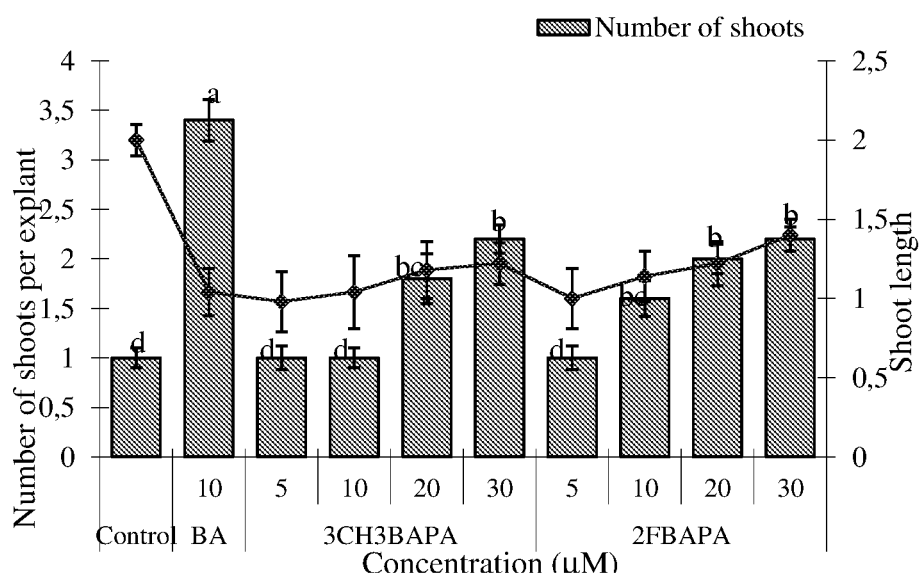
FIG. 2: Effect of BA, 3CH3BAPA and 2FBAPA on shoot multiplication of *Dais cotinifolia*. The results are expressed as the means with SEM from three replicates per treatment. The data were recorded after 8 weeks of culture. Means±SEM followed by same letter are not significantly different at the 5% level as determined by Duncan's multiple range test (Example 16).
Figure 3:
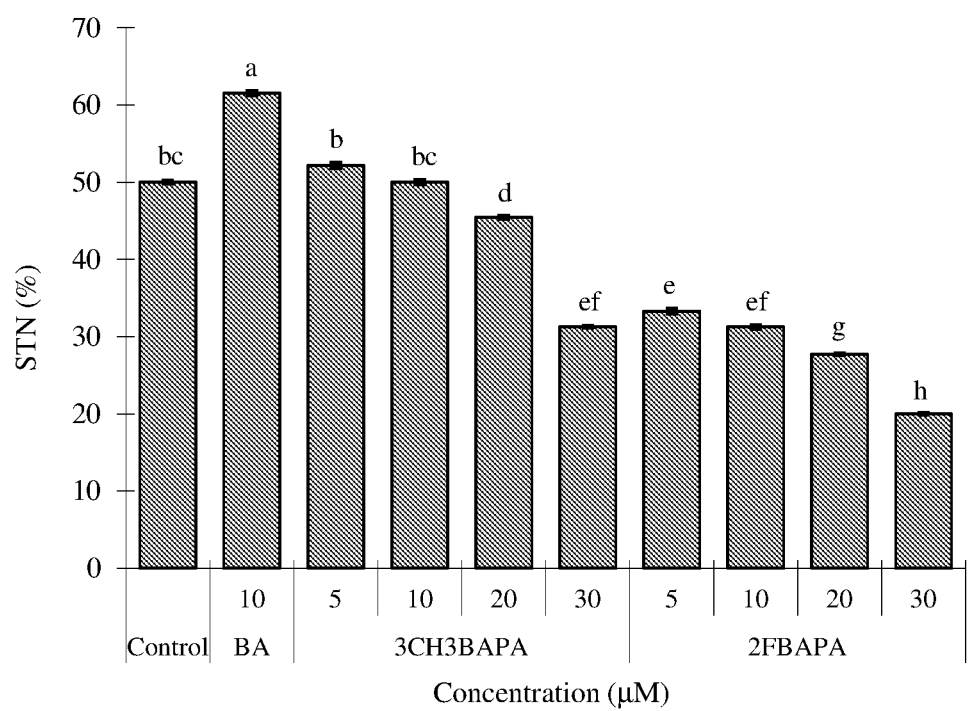
FIG. 3 Effect of BA, 3CH3BAPA and 2FBAPA on shoot-tip necrosis of *Dais cotinifolia*. The results are expressed as the means with SEM from three replicates per treatment. The data were recorded after 8 weeks of culture. Means±SEM followed by same letter are not significantly different at the 5% level as determined by Duncan's multiple range test. STN=Shoot-tip necrosis (Example 16).

Example 1: Synthesis of 6-(3-methoxybenzylamino)-9-β-D-arabinofuranosylpurine 9-(β-D-arabinofuranosyl) hypoxantine (100 mg, 0.37 mmol), (benzotriazol-1-yloxy)tris(dimethylamino)phosphonium hexafluorophosphate (BOP, 196 mg, 0.44 mmol) and N,N-diisopropylethylamine (DIPEA, 97 µl, 0.56 mmol) were mixed in dimethylformamide (DMF, 1.86 ml). Subsequently, 3-methoxybenzylamine (56 µl, 0.56 mmol) was added. 9-(β-D-arabinofuranosyl) hypoxantine is commercially available (Jena Bioscience, N-1002) or can be prepared from 9-(β-D-arabinofuranosyl) adenine. Reaction mixture was mixed at laboratory temperature (25° C.) under argon overnight (16 hrs). After that period, reaction mixture was evaporated on vacuum rotary evaporator and one of the following procedures was used to obtain the crude product: First, the reaction mixture was purified by column liquid chromatography (mobile phase chloroform-methanol 19:1) or cold water was slowly added (15 ml) and the reaction mixture was vortexed: a yellowish substance started to occur after a few minutes. Reaction mixture was than placed into the fridge and left overnight. Arising product was filtrated and once recrystallized from isopropanol and twice from ethanol. Final product is a white crystalline solid. Both ways of isolation of the product described above gave 40% yield, TLC (40% chlorform:metanol (90:10, v:v): one spot; HPLC purity>98%. [M+H$^+$]388, $^1$H (DMSO-d$_6$, 300 MHz) δ ppm: 3.65-3.66 (m, 2H), 3.70 (s, 3H), 3.78 (d, J=3.7 Hz), 4.14 (s, 2H), 4.67 (bs, 2H), 5.09 (t, J=5.3 Hz), 5.52 (d, J=3.8 Hz), 5.61 (d, J=4.5 Hz), 6.27 (d, J=3.9 Hz), 6.77 (d, J=7.1 Hz), 6.89 (s, 1H), 6.91 (s, 1H), 7.20 (t, J=7.6 Hz), 8.19 (s, 1H), 8.21 (s, 1H), 8.34 (bs, 1H).

Example 2: Synthesis of 6-(3-hydroxybenzylamino)-9-β-D-arabinofuranosylpurine 9-(β-D-arabinofuranosyl) hypoxantine (100 mg, 0.37 mmol), BOP (196 mg, 0.44 mmol) and DIPEA (97 µl, 0.56 mmol) were mixed in v DMF (1.86 ml). Subsequently, 3-hydroxybenzylamine (50 µl, 0.50 mmol) was added. 9-(β-D-arabinofuranosyl) hypoxantine is commercially available (Jena Bioscience, N-1002). Reaction mixture was mixed under argon atmosphere at laboratory temperature (25° C.) overnight (10 hrs). Reaction mixture was evaporated using vacuum rotary evaporator and purified by column liquid chromatography (mobile phase chlorform: methanol 19/1). Product is a white crystalline solid, yield 5%, TLC (chlorform:metanol (90:10, v:v): one spot; HPLC purity>98%, [M+H$^+$]374, NMR: $^1$H (DMSO-d$_6$, 300 MHz) δ ppm: 3.66 (s, 2H), 3.78 (s, 1H), 4.15 (s, 2H), 4.63 (bs 2H), 5.12 (s, 1H), 5.55 (s, 1H), 5.64 (s, 1H), 6.28 (s, 1H), 6.58 (d, J=7.5 Hz), 6.73 (s, 1H), 6.76 (s, 1H), 7.07 (t, J=7.5 Hz), 8.19 (s, 1H), 8.21 (s, 1H), 9.27 (bs, 1H).

Example 3: Synthesis of 6-(3-fluorobenzylamino)-9-β-D-arabinofuranosylpurine 9-(β-D-arabinofuranosyl) hypoxantine (100 mg, 0.37 mmol), BOP (196 mg, 0.44 mmol) and DIPEA (97 µl, 0.56 mmol) were mixed together in DMF (1.86 ml) and subsequently, 3-fluorbenzylamine (70 µl, 0.76 mmol) was added. 9-(β-D-arabinofuranosyl) hypoxantine was prepared from commercially available 9-(β-D-arabinofuranosyl)adenine. Reaction mixture was mixed under argon at laboratory temperature of 25° C. for 24 h. Reaction mixture was evaporated on vacuum rotary evaporator and cold water was added after small portions of 15 ml. After several minutes of vortexing, yellowish substance started to occur. Reaction mixture was then refrigerated for 10 hrs. A product was filtered off and once recrystallized using isopropanol and twice using ethanol. Produkt is a white crystalline solid, in both cases of isolation, the yield 70%, TLC (chlorform: metanol (90:10, v:v): one spot; HPLC purity>98%. [M+H$^+$] 376, NMR: $^1$H (DMSO-d$_6$, 300 MHz) δ ppm: 3.66 (s, 2H), 3.79 (s, 1H), 4.14 (s, 2H), 4.74 (bs, 2H), 5.09 (s, 1H), 5.50 (s, 1H), 5.60 (s, 1H), 6.29 (s, 1H), 7.17 (s, 4H), 8.22 (s, 2H), 8.37 (bs, 1H).

Example 4: Synthesis of 6-(3-iodobenzylamino)-9-β-D-arabinofuranosylpurine 9-(β-D-arabinofuranosyl) hypoxantine (100 mg, 0.37 mmol), BOP (196 mg, 0.44 mmol) were mixed together in DMF (2 ml) and subsequently, 3-iodobenzylamine (60 µl) and DIPEA (97 µl) was added. 9-(β-D-arabinofuranosyl) hypoxantine was prepared from commercially available 9-(β-D-arabinofuranosyl)adenine. Reaction mixture was mixed under argon atmosphere in oil bath at the temperature of 60° C. for 24 h. Reaction mixture was evaporated on vacuum rotary evaporator. Arising gel was absorbed to silicagel and chromatography columns was used for sample purification using chloroform:methanol mobile phase with the gradient 99:1 to 9:1. TLC (chlorform:metanol (90:10, v:v): one spot; HPLC purity>98%. [M+H$^+$] 484, NMR: $^1$H (DMSO-d$_6$, 300 MHz) δ ppm: $^1$H (DMSO-d$_6$, 500 MHz) δ ppm: 3.6 (s, 1H), 3.7 (s, 1H), 3.76-3.81 (m, 2H), 4.09-4.17 (m, 2H), 4.64 (bs, 1H), 5.23 (bs, 1H), 5.66 (bs, 2H), 6.24 (d, J=5 Hz, 1H), 7.09 (t, J=7.5 Hz, 1H), 7.34 (d, J=7.5 Hz, 1H), 7.55 (d, J=8 Hz, 1H), 7.69 (s, 1H), 8.18 (s, 1H), 8.21 (s, 1H), 8.37 (bs, 1H)

Example 5: Synthesis of 6-furfurylamino-9-β-D-arabinofuranosylpurine 6-chloropurine tetraacetylarabinopyranoside (100 mg, 0.242 mmol) dispersed in methanol (3 ml) was placed into microwave reactor CEM SP reaction vessel (10 ml). Subsequently, furfurylamine (26.8 µl, 0.291 mmol) with triethylamine (151 µl, 1.09 mmol) were added. Reaction conditions were adjusted as follows: dynamic method, it means: reaction time 3 hrs, temperature: 100° C., pressure 100 psi and performance: 50 watt. Reaction mixture was evaporated using vacuum rotary evaporator and purified using column liquid chromatography (mobile phase: chloroform:methanol 9/1). The product is a white solid: kinetin arabinopyranoside, mixture of α and β anomers in ration 5/1. The anomers were separated from each other: yield: 30% of α anomer and 10% of β anomer. Starting compound 6-chloropurine tetraacetylarabinopyranoside was prepared as follows: 6-chloropurine (0.412 g, 2.66 mmol) was placed into a dry flask and a tetraacetylarabinose (0.771 g 2.42 mmol) dissolved in dry acetonitrile was added through the septum by a needle (15 ml). Subsequently, tin tetrachloride was slowly added by a needle (5.6 mmol 0.6 ml). Reaction mixture was mixed at laboratory temperature under argon overnight. After that period, a mixture was evaporated using vacuum evaporator and ethylacetate (25 ml) was added. Organic phase was extracted by sodium carbonate solution (30 ml) and water (2×30 ml) and after that dried over sodium sulphate and again evaporated using vacuum evaporator. A product was purified by column liquid chromatography, mobile dichlormethane-aceton 9/1. As the result after the evaporation of organic solvents, there occurred clear gel like residue and this residue was mixed with diethyl ether and changed into a white solid 6-chloropurine tetraacetylarabinopyranosid, a mixture of α and β anomers. Yield: 50%, HPLC purity: 98%, [M+H$^+$] 348, NMR: $^1$H (DMSO-d$_6$, 300 MHz) δ ppm: 3.61-3.72 (m, 2H), 3.78 (d, J=3.9 Hz), 4.14 (s, 2H), 4.69 (bs, 2H), 5.11 (t, J=5.4 Hz), 5.54 (d, J=3.9 Hz), 5.62 (d, J=4.8 Hz), 6.22 (d, J=2.7 Hz), 6.27 (d, J=4.2 Hz), 6.36 (t, J=3.0 Hz), 7.54 (s, 1H), 8.21 (s, 3H).

Example 6: Synthesis of 6-(2-chlorobenzylamino)-9-β-D-arabinofuranosylpurine 9-(β-D-arabinofuranosyl) hypoxantine (100 mg, 0.37 mmol), BOP (196 mg, 0.44 mmol) were mixed together in DMF (2 ml) and subsequently, 2-chlorobenzylamine (55 µl) and DIPEA (97 µl) was added. Reaction mixture was mixed under argon atmosphere in oil bath at the temperature of 60° C. for 24 h. Reaction mixture was evaporated on vacuum rotary evaporator. MeOH with a drop of chloroform was added to distillation residue and the mixture was ultrasonised. The process formed arising of a white paste solid that was filtrated. The resulted white solid was re-crystallized from EtOH and left in refrigerator overnight. Result was a white solid. TLC (chlorform:metanol (90:10, v:v): one spot; HPLC purity>98%. [M+H$^+$] 392, NMR: $^1$H (DMSO-d$_6$, 300 MHz) δ ppm: $^1$H (DMSO-d$_6$, 500 MHz) δ ppm: 3.60-3.71 (m, 2H), 3.77 (q, J=4 Hz, 1H), 4.11-4.15 (m, 2H), 4.69 (bs, 2H), 5.14 (bs, 1H), 5.57 (bs, 2H), 6.25 (d, J=4.5 Hz, 1H), 7.25-7.33 (m, 3H), 7.36 (s, 1H), 8.18 (s, 1H), 8.21 (s, 1H), 8.40 (bs, 1H).

Example 7: The synthesis of 6-(2-aminobenzylamino)-9-β-D-arabinofuranosylpurine 9-(β-D-arabinofuranosyl) hypoxantine (100 mg, 0.37 mmol), BOP (196 mg, 0.44 mmol) were mixed together in DMF (2 ml) and subsequently, 2-aminobenzylamine (55 µl) and DIPEA (97 µl) was added. Reaction mixture was mixed under argon atmosphere in oil bath at the temperature of 60° C. for 24 h. Reaction mixture was evaporated on vacuum rotary evaporator. The resulted distillation residue was re-crystallized from EtOH and left in refrigerator overnight. Result was a white solid that was filtrated off and dried. TLC (chlorform:metanol (90:10, v:v): one spot; HPLC purity>98%, NMR: $^1$H (DMSO-d$_6$, 300 MHz) δ ppm: $^1$H (DMSO-d$_6$, 500 MHz) δ ppm: 3.59-3.70 (m, 2H), 3.77 (q, J=4 Hz, 1H), 4.11-4.15 (m, 2H), 4.51 (bs, 2H), 5.10 (t, J=5.5 Hz, 1H), 5.20 (s, 2H), 5.52 (d, J=4 Hz, 1H), 5.60 (d, J=5 Hz, 1H), 6.26 (d, J=4 hz, 1H), 6.46 (t, J=7.5 Hz, 1H), 6.59 (d, J=8 Hz, 1H), 6.91 (t, J=7.5 Hz, 1H), 7.07 (d, J=7.5 Hz, 1H), 8.19 (s, 3H)

TABLE 1

6-substituted-9-β-D-arabinofuranosylpurines prepared by the method according to Examples 1-7, elemental analyses and ES-MS measurement results of these compounds

| Substituent in position 6 (—NH—Ar) | Elemental analysis calculated/found | | | ES-MS [M + H$^+$] |
|---|---|---|---|---|
| | % C | % H | % N | |
| furfurylamino | 51.9/51.6 | 4.9/4.8 | 20.2/20.2 | 348 |
| 2-fluorobenzylamino | 54.4/54.1 | 4.8/4.8 | 18.7/18.4 | 376 |
| 3-fluorobenzylamino | 54.4/53.9 | 4.8/4.7 | 18.7/18.2 | 376 |
| 4-fluorobenzylamino | 54.4/54.3 | 4.8/4.8 | 18.7/18.3 | 376 |
| 2-chlorobenzylamino | 52.1/52.0 | 4.6/4.7 | 17.9/17.5 | 392 |
| 3-chlorobenzylamino | 52.1/51.9 | 4.6/4.6 | 17.9/17.3 | 392 |
| 4-chlorobenzylamino | 52.1/51.8 | 4.6/4.5 | 17.9/17.1 | 392 |
| 2-bromobenzylamino | 46.8/46.3 | 4.2/4.1 | 16.1/15.5 | 437 |
| 3-bromobenzylamino | 46.8/47.8 | 4.2/4.5 | 16.1/15.6 | 437 |
| 4-bromobenzylamino | 46.8/46.4 | 4.2/4.3 | 16.1/15.4 | 437 |
| 3-iodobenzylamino | 42.3/42.4 | 3.8/3.9 | 14.5/14.6 | 484 |
| 4-iodobenzylamino | 42.3/42.4 | 3.8/3.8 | 14.5/14.7 | 484 |
| 2-methylbenzylamino | 58.2/58.0 | 5.7/5.8 | 18.9/19.1 | 372 |
| 3-methylbenzylamino | 58.2/58.0 | 5.7/5.7 | 18.9/19.0 | 372 |
| 4-methylbenzylamino | 58.2/57.9 | 5.7/5.8 | 18.9/19.1 | 372 |
| 2-aminobenzylamino | 54.8/55.0 | 5.4/5.6 | 22.6/22.7 | 373 |
| 3-aminobenzylamino | 54.8/55.2 | 5.4/5.5 | 22.6/22.8 | 373 |
| 4-aminobenzylamino | 54.8/55.1 | 5.4/5.5 | 22.6/22.7 | 373 |
| 2-methoxybenzylamino | 55.8/55.9 | 5.5/5.3 | 18.1/17.9 | 388 |
| 3-methoxybenzylamino | 55.8/55.5 | 5.5/5.7 | 18.1/18.0 | 388 |
| 4-methoxybenzylamino | 55.8/55.6 | 5.5/5.5 | 18.1/18.1 | 388 |
| 2-hydroxybenzylamino | 54.7/54.6 | 5.1/5.0 | 18.8/18.8 | 374 |
| 3-hydroxybenzylamino | 54.7/54.5 | 5.1/5.1 | 18.8/18.5 | 374 |

TABLE 1-continued 6-substituted-9-β-D-arabinofuranosylpurines prepared by the method according to Examples 1-7, elemental analyses and ES-MS measurement results of these compounds

| Substituent in position 6 (—NH—Ar) | Elemental analysis calculated/found | | | ES-MS [M + H⁺] |
|---|---|---|---|---|
| | % C | % H | % N | |
| 4-hydroxybenzylamino | 54.7/54.6 | 5.1/4.9 | 18.8/18.6 | 374 |
| 2,4-dichlorobenzylamino | 47.9/47.8 | 4.0/4.1 | 16.4/16.5 | 427 |
| 3,4-dichlorobenzylamino | 47.9/47.9 | 4.0/4.2 | 16.4/16.5 | 427 |
| 2,3-dihydroxybenzylamino | 52.4/52.5 | 4.9/4.8 | 18.0/18.1 | 390 |
| 3,5-dihydroxybenzylamino | 52.4/52.6 | 4.9/4.9 | 18.0/18.3 | 390 |
| 2-hydroxy-3-methoxybenzylamino | 53.6/53.4 | 5.2/5.1 | 17.4/17.5 | 404 |
| 3-hydroxy-4-methoxybenzylamino | 53.6/53.5 | 5.2/5.0 | 17.4/17.6 | 404 |
| 2,3-dimethoxybenzylamino | 54.7/54.8 | 5.6/5.7 | 16.8/16.7 | 418 |
| 2,4-dimethoxybenzylamino | 54.7/54.6 | 5.6/5.5 | 16.8/16.6 | 418 |
| 3,4-dimethoxybenzylamino | 54.7/54.8 | 5.6/5.6 | 16.8/16.5 | 418 |
| 3,5-dimethoxybenzylamino | 54.7/54.6 | 5.6/5.7 | 16.8/16.9 | 418 |

Example 8: The synthesis of 6-(3-methoxybenzylamino)-9-β-D-arabinofuranosylpurine in bench scale Feedstock: 9-β-D-Arabinofuranosyl-hypoxanthine (1072 g, 4 mol),
(Benzotriazol-1-yloxy)tris(dimethylamino)phosphonium hexafluorophosphate (BOP, 2124 g (4.8 mol), dimethylformamide (DMF, 20 L, N,N-Diisopropyl-N-ethylamine (DIPEA, 1045 mL (6 mol), 3-methoxybenzylamine (658 g, 4.8 mol), demi water 40 l, 2-propanol 30 L.
Procedure:
Dimethylformamide (20 l) was placed into a glass duplicated reactor A1 equiped with thermometer (PT100) and reflux condenser. Reactor was filled in with inert atmosphere (nitrogen). Stirring with hopper opening was switched on. 9-β-D-arabinoturanosyl hypoxanthine and BOP (2124 g) were poured to the reactor using the respirator. As soon as the solid is dissolved, DIPEA (1045 mL) and 3-methoxybenzylamine (658 g) were added. The reactor stayed under continuous mild nitrogen flow. Reaction mixture was heated (using duplication) to 50° C., and was stirred for 20 hrs. Reaction course control: after 12 hrs of reaction, sample for TLC: 1 ml aliquot was dilluted by 4 ml of methanol and the solution was applied next to the other starting compounds and standard product on TLC plate. TLC plate was evolved in the following mobile phase: chloroform:methanol:ammonium water solution; 4:1:0.05). If the reaction was still not finished, the mixture was further stirred at 50° C., but next portion of BOP could be also added (200 g). If the reaction was finished (>90%), reaction mixture was cooled (via duplication) to the temperature of 20-25° C. and after that was reaction mixture drained into the transport vessel. Reactor was subsequently splashed with a small amount of methanol (3×1 L), and methanolic portions were mixed with reaction mixture). Reaction mixture was evaporated on rotary evaporator—a vacuum was secured by water ring vacuum pump—parameters such as pressure and temperature were established according to technolog instructions. Distillation residue was (hot) drained into transport vessel. Evaporator was splashed with hot methanol—and this portion was evaporated using vacuum evaporator separately from the main portion. Reactor A1 was filled with demi water (40 L), stirring and cooling in duplication was switched on. Reactor was cooled to 10° C. and distillation residue was slowly added. Transport vessel was splashed with methanol (3×250 mL) and methanolic solution was also poured into the reactor. The reactor content was stirred for three hours at 10-15° C. Emerging precipitate was filtered off on great Buchner channel and washed first with cold water (+5° C.) than only by water (4×1 L). Crude product was dried in a convection oven at 80° C. Yield: 1200-1250 g.

Crystallization of 6-(3-methoxybenzylamino)-9-β-D-arabinofuranosylpurine

Crude product: 1000 g, 2-propanol: 18 l, active carbon CXV 50 g

Procedure: 2-propanol (15 l) was poured into A1 reactor and stirring was switched on. Crude 6-(3-methoxybenzylamino)-9-β-D-arabinofuranosylpurin (1000 g) was added. The content or reactor was heated via duplication to 80° C.—the solid of crude product should be dissolved. If the product was not dissolved, it is necessary to continue stirring at 80° C., or add next portion of 2-propanol. As soon as was all solid dissolved, active carbon was added and stirring is continued at 80° C. for 15 minutes. After that, the solution was filtrated off using preheated Büchner channel (preheated in convection oven, 110° C.). Glass reactor was rinsed by 2-propanol (2×1 L) and filtration cake was washed with this portion of 2-propanol Büchner chanell. Filtrate and flushing were merged together and placed into transport vessel for crystallization. Product crystallized at the temperature of +5-+10° C. for 12 hrs. After the solid appeared, the product was filtrated off, rinsed with cold (+5° C.) 2-propanol (3×500 mL) and dried in convection oven at 70° C. to constant weight. Yield: 750-800 g, HPLC purity: >98%.

Example 9: Synthesis of 6-(3-methoxybenzylamino)-9-β-D-2'-deoxyribofuranosylpurine 2'-deoxyinosine (252 mg) and BOP (531 mg) were dissolved in dry DMF (5 ml) and stirred at laboratory temperature under argon atmosphere. After five minutes, DIPEA (261 µl) and 3-methoxybenzylamine (167 µl) were added. Reaction mixture was stirred at laboratory temperature for 16 hrs. Reaction process was controlled via TLC (mobile phase: chloroform-methanol-25% aqueous ammonia, 4:1:0.05). As soon as the conversion was not complete, next portion BOP (354 mg; 0.8 mmol) was added and reaction mixture was heated to 60° C. and stirred for 6 hrs. As soon as there were not detected a spot of starting 2'-deoxyinosine, reaction mixture was evaporated using vacuum evaporator (maximal temperature 55° C.). A residue (cca 1.5 g) was chromatographically purified using silica gel (150 g); mobile phase: 0-20% methanol in dichlormethane. Yield: 270 mg (79%), HPLC-MS purity: 98+%, [1\4+H⁺] 372, mp 165-170° C., C/H/N: 58.2/58.1; 5.7/5.7; 18.9/18.8; $^1$H (DMSO-$d_6$, 300 MHz) δ ppm: 2.25-2.37 (m, 1H), 2.45-2.64 (m, 1H), 3.50-3.68 (m, 2H), 3.70 (s, 3H), 3.85-3.90 (m, 1H), 4.33-4.45 (m, 1H), 4.67 (bs, 2H), 4.85 (t, 1H), 5.10 (d, J=4.0 Hz), 6.30 (t, J=6.9 Hz), 6.77 (d, J=7.1 Hz), 6.89 (s, 1H), 6.91 (s, 1H), 7.20 (t, J=7.6 Hz), 8.19 (s, 1H), 8.21 (s, 1H), 8.34 (bs, 1H).

Example 10: Synthesis of 6-(2-hydroxybenzylamino)-9-β-D-2'-deoxyribofuranosylpurine 2'-deoxyinosine (252 mg) and BOP (664 mg) were dissolved in dry DMF (8 ml) and stirred at laboratory temperature under argon atmosphere. After five minutes, DIPEA (348 µl) and 2-hydroxybenzylamine (131 µl) were added. Reaction mixture was stirred at 50° C. for 20 hrs. Reaction process was controlled via TLC (mobile phase: chloroform-methanol-25% aqueous ammonia, 4:1:0.05). As soon as the conversion was not complete, next portion BOP (354 mg; 0.8 mmol) was added and reaction mixture was heated to 60° C. and stirred for 10 hrs. As soon as there were not detected a spot of starting 2'-deoxyinosine, reaction mixture was evaporated using vacuum evaporator (maximal temperature 55° C.). A residue (cca 1.5 g) was chromatographically purified using silica gel (150 g); mobile phase: 0-20% methanol in dichlormethane. Yield: 250 mg (70%), HPLC-MS purity: 98+%, [M+H$^+$] 358, mp 172-175° C., C/H/N: 57.1/57.2; 5.3/5.4; 19.6/19.2; $^1$H (DMSO-d$_6$, 300 MHz) δ ppm: 3.66 (s, 2H), 3.78 (s, 1H), 4.15 (s, 2H), 4.63 (bs 2H), 5.12 (s, 1H), 5.55 (s, 1H), 5.64 (s, 1H), 6.28 (s, 1H), 6.58 (d, J=7.5 Hz), 6.73 (s, 1H), 6.76 (s, 1H), 7.07 (t, J=7.5 Hz), 8.19 (s, 1H), 8.21 (s, 1H), 9.27 (bs, 1H).

Example 11: Synthesis of 6-(2-hydroxy-3-methoxybenzylamino)-9-β-D-2'-deoxyribofuranosylpurine 2'-deoxyinosine (252 mg) and BOP (664 mg) were dissolved in dry DMF (10 ml) and stirred at 50° C. After five minutes, DIPEA (348 µl) and 2-hydroxy-3-methoxybenzylamine (165 µl) were added. Reaction mixture was stirred at laboratory temperature for at least 20 hrs. Reaction process was controlled via TLC (mobile phase: chloroform-methanol-25% aqueous ammonia, 4:1:0.05). As soon as the conversion was not complete, next portion BOP (354 mg; 0.8 mmol) was added and reaction mixture was heated to 70° C. and stirred for 6 hrs. As soon as there were not detected a spot of starting 2'-deoxyinosine, reaction mixture was evaporated using vacuum evaporator (maximal temperature 55° C.). A residue (cca 1.5 g) was chromatographically purified using silicagel (150 g); mobile phase: 0-20% methanol in dichlormethane. Yield: 270 mg (79%), HPLC-MS purity: 98+%, mp 174-178° C., [M+H$^+$] 388, C/H/N: 55.8/55.3; 5.5/5.6; 18.1/18.2; $^1$H (DMSO-d$_6$, 300 MHz) δ ppm: 2.25-2.37 (m, 1H), 2.45-2.64 (m, 1H), 3.50-3.68 (m, 2H), 3.77 (s, 3H), 3.85-3.90 (m, 1H), 4.33-4.45 (m, 1H), 4.67 (bs, 2H), 4.85 (t, 1H), 5.10 (d, J=4.0 Hz), 5.39 (d, J=6.0 Hz), 6.30 (t, J=6.9 Hz), 6.77 (d, J=7.1 Hz), 6.89 (s, 1H), 7.20 (t, J=7.6 Hz), 8.19 (s, 1H), 8.21 (s, 1H), 8.34 (bs, 1H).

Example 12: Synthesis of 6-(furfurylamino)-9-β-D-2'-deoxyribofuranosylpurine

2'-deoxyinosine (252 mg) and BOP (670 mg) were dissolved in dry DMF (10 ml) and stirred at laboratory temperature under argon atmosphere. After five minutes, DIPEA (350 µl) and furfurylamine (150 µl) were added. Reaction mixture was stirred at 60° C. for at least 10 hrs. Reaction process was controlled via TLC (mobile phase: chloroform-methanol-25% aqueous ammonia, 4:1:0.05). As soon as the conversion was not complete, next portion BOP (354 mg; 0.8 mmol) was added and reaction mixture was heated to 70° C. and stirred for 6 hrs. As soon as there were not detected a spot of starting 2'-deoxyinosine, reaction mixture was evaporated using vacuum evaporator (maximal temperature 55° C.). A residue (cca 1.5 g) was chromatographically purified using silica gel (150 g); mobile phase: 0-20% methanol in dichlormethane. Yield: 300 mg (82%), HPLC-MS purity: 98+%, [M+H$^+$] 332, C/H/N: 54.4/54.3; 5.2/5.2; 19.3/19.5 $^1$H (DMSO-d$_6$, 300 MHz) δ ppm: 3.61-3.72 (m, 2H), 3.78 (d, J=3.9 Hz), 4.14 (s, 2H), 4.69 (bs, 2H), 5.11 (t, J=5.4 Hz), 5.54 (d, J=3.9 Hz), 5.62 (d, J=4.8 Hz), 6.22 (d, J=2.7 Hz), 6.27 (d, J=4.2 Hz), 6.36 (t, J=3.0 Hz), 7.54 (s, 1H), 8.21 (s, 3H).

TABLE 2

6-substituted-9-β-D-2'-deoxyribofuranosylpurines prepared according to examples 9-12

| Substituent in position 6 (—NH—Ar) | Elemental analysis calculated/found | | | ES-MS [M + H$^+$] |
|---|---|---|---|---|
| | % C | % H | % N | |
| 4-methylfurfurylamino | 55.6/55.5 | 5.5/5.6 | 18.5/18.4 | 346 |
| 5-methylfurfurylamino | 55.6/55.4 | 5.5/5.6 | 18.5/18.3 | 346 |
| 4-hydroxyfurfurylamino | 51.9/51.8 | 4.9/5.0 | 20.2/20.1 | 348 |
| 5-hydroxyfurfurylamino | 51.9/52.0 | 4.9/4.8 | 20.2/20.2 | 348 |
| 3-chlorobenzylamino | 54.3/54.2 | 4.8/4.8 | 18.6/18.6 | 376 |
| 4-chlorobenzylamino | 54.3/54.3 | 4.8/4.9 | 18.6/18.5 | 376 |
| 2-bromobenzylamino | 48.6/48.7 | 4.3/4.4 | 16.7/16.7 | 421 |
| 3-bromobenzylamino | 48.6/48.6 | 4.3/4.5 | 16.7/16.8 | 421 |
| 4-bromobenzylamino | 48.6/48.3 | 4.3/4.3 | 16.7/16.9 | 421 |
| 2-methoxybenzylamino | 58.2/58.3 | 5.7/5.5 | 18.9/18.6 | 372 |
| 3-methoxybenzylamino | 58.2/58.1 | 5.7/5.9 | 18.9/18.7 | 372 |
| 2-hydroxybenzylamino | 57.1/57.2 | 5.4/5.3 | 19.6/19.8 | 358 |
| 3-hydroxybenzylamino | 57.1/57.3 | 5.4/5.3 | 19.6/19.5 | 358 |
| 4-hydroxybenzylamino | 57.1/57.1 | 5.4/5.2 | 19.6/19.5 | 358 |
| 2,3-dihydroxybenzylamino | 54.7/54.5 | 5.1/5.2 | 18.8/18.7 | 374 |
| 3,5-dihydroxybenzylamino | 54.7/54.8 | 5.1/5.3 | 18.8/18.6 | 374 |
| 2-hydroxy-3-methoxybenzylamino | 55.8/55.7 | 5.5/5.6 | 18.1/18.2 | 388 |
| 3-hydroxy-4-methoxybenzylamino | 55.8/55.6 | 5.5/5.7 | 18.1/18.3 | 388 |
| 2,3-dimethoxybenzylamino | 56.9/56.8 | 5.8/5.7 | 17.5/17.4 | 402 |
| 2,4-dimethoxybenzylamino | 56.9/56.9 | 5.8/5.6 | 17.5/17.5 | 402 |
| 3,4-dimethoxybenzylamino | 56.9/56.8 | 5.8/5.9 | 17.5/17.7 | 402 |
| 3,5-dimethoxybenzylamino | 56.9/56.9 | 5.8/5.9 | 17.5/17.8 | 402 |

Example 13: Evaluation of Cytotoxicity of Novel Derivatives for Skin Cell by MTT In Vitro Test MTT assay is a standard test of toxicity based on photometric measurement of the ability of metabolically active cells to reduce MTT (3-(4,5-dimethylthiazol-2-yl)-2,5-diphenyltetrazolium bromide). Using the assay, the effects of 72 hour treatments with several concentrations of the compounds (sixfold dilution, maximal concentration=50 microM) on viability of skin fibroblasts BJ and keratinocytes HaCaT were evaluated. About 5,000 cells were seeded per well of a 96-well plate 24 hours before the treatment. DMSO vehiculum was used as a negative control. After 72 hour treatment, new medium with MTT (Sigma, M2128) was added to a final concentration of 0.5 mg/ml. After 3 hours, medium was removed and resulting formazan in the cells was dissolved in DMSO. The absorbance was measured at 570 nm (640 nm reference wavelength). The IC50 values were calculated from the dose-response curves. 6-Benzylaminopurine riboside and 6-furfurylaminopurine riboside were used as positive controls they were toxic in the MTT test. The following results were obtained.

| | IC50 (µM) |
|---|---|
| dimethylsulfoxide | >50 |
| 6-benzylamino-9-β-D-arabinofuranosylpurine | >50 |

-continued

| | IC50 (μM) |
|---|---|
| 6-furfurylamino-9-β-D-arabinofuranosylpurine | >50 |
| 6-(3-methoxybenzylamino)-9-β-D-arabinofuranosylpurine | >50 |
| 6-(2-chlorobenzylamino)-9-β-D-arabinofuranosylpurine | >50 |
| 6-(3-hydroxybenzylamino)-9-β-D-arabinofuranosylpurine | >50 |
| 6-(3-chlorobenzylamino)-9-β-D-arabinofuranosylpurine | >50 |
| 6-(2,3-dimethoxybenzylamino)-9-β-D-arabinofuranosylpurine | 49 |
| 6-(2,3,4-trimethoxybenzylamino)-9-β-D-arabinofuranosylpurine | 48 |
| 6-(3-iodobenzylamino)-9-β-D-arabinofuranosylpurine | >50 |
| 6-(3-aminobenzylamino)-9-β-D-arabinofuranosylpurine | >50 |
| 6-(furfurylamino)-9-β-D-2'-deoxyribofuranosylpurine | >50 |
| 6-(2-hydroxybenzylamino)-9-β-D-2'-deoxyribofuranosylpurine | >50 |
| 6-benzylaminopurin9-ribosylpurine (comparative example) | ≤3 |
| 6-furfurylamino-9-ribosylpurine (comparative example) | ≤3 |

The results show that the novel compounds are not cytotoxic for animal/human cells, and thus are safe for use in agriculture and do not present danger for consumers.

Example 14: SRB In Vitro Toxicity Test

SRB (sulforhodamine B) assay is a standard toxicity test based on a photometric measurement of the cellular protein content after the staining with sulphorhodamine B. Using the assay, the effects of 72 hour treatments with several concentrations of the compounds (sixfold dilution, maximal concentration=50 microM) on viability of skin fibroblasts BJ and keratinocytes HaCaT were evaluated. About 5,000 cells were seeded per well of a 96-well plate 24 hours before the treatment. DMSO vehiculum was used as a negative non-toxic control. 6-benzylaminopurine riboside a 6-furfurylaminopurin riboside were used as positive toxic controls. After three days the medium was removed and the cells fixed with 10% (wt/vol) trichloroacetic acid. After the extensive washing in distilled water, 0.4% (wt/vol) solution of SRB in acetic acid was added and the fixed cells were stained for 30 minutes. The unbound stain was washed away by distilled water and the bound SRB was solubilized in unbuffered 10 mM Tris base. Absorbance was measured at 564 nm. IC50 values were calculated from dose-response curves.

The following results were obtained:

| | IC 50 (μM) |
|---|---|
| dimethylsulfoxide | >50 |
| 6-benzylaminopurine-9-β-D-arabinofuranosylpurine | >50 |
| 6-furfurylamino-9-β-D-arabinofuranosylpurine | >50 |
| 6-(3-methoxybenzylamino)-9-β-D-arabinofuranosylpurine | >50 |
| 6-(2-chlorobenzylamino)-9-β-D-arabinofuranosylpurine | >50 |
| 6-(3-hydroxybenzylamino)-9-β-D-arabinofuranosylpurine | >50 |
| 6-(3-chlorobenzylamino)-9-β-D-arabinofuranosylpurine | 48 |
| 6-(3-iodobenzylamino)-9-β-D-arabinofuranosylpurine | >50 |
| 6-(3-aminobenzylamino)-9-β-D-arabinofuranosylpurine | >50 |
| 6-(furfurylamino)-9-β-D-2'-deoxyriboside | >50 |
| 6-(2-hydroxybenzylamino)-9-β-D-2'-deoxyriboside | >50 |
| 6-(2,3-dimethoxybenzylamino)-9-β-D-arabinofuranosylpurine | >50 |
| 6-(2,3,4-trimethoxybenzylamino)-9-β-D-arabinofuranosylpurine | >50 |
| 6-furfurylamino-9-ribosylpurine (comparative example) | ≤3 |

The results show that the novel compounds are not cytotoxic for animal/human cells, and thus are safe for use in agriculture and do not present danger for consumers.

Example 15: Anti-Senescent Activity of Novel Compounds Tested in Senescent Bioassay on Wheat Leaf Segments Seeds of winter wheat, Triticum aestivum cv. Hereward, were washed under running water for 24 hours and then sown on vermiculite soaked with Knop's solution. They were placed in the growth chamber at 25° C. with a 16/8 h light period at 50 μmol·m$^{-2}$·s$^{-1}$. After 7 days, the first leaf was fully developed and the second leaf had started to grow. A tip section of the first leaf, approximately 35 mm long, was removed from 5 seedlings and trimmed slightly to a combined weight of 100 mg. The basal ends of the five leaf tips were placed in the wells of a microtiter polystyrene plate containing 150 μL of the tested derivative solution each. The entire plate was inserted into a plastic box lined with paper tissues soaked in distilled water to prevent leaf sections from drying out. After 96 h incubation in the dark at 25° C., the leaves were removed and chlorophyll extracted by heating at 80° C. for 10 min in 5 mL of 80% ethanol (v/v). The sample volume was then restored to 5 mL by the addition of 80% ethanol (v/v). The absorbance of the extract was recorded at 665 nm. In addition, chlorophyll extracts from fresh leaves and leaf tips incubated in deionised water were measured. The results are means of five replicates and the entire test was repeated twice. In each experiment activities of the novel compounds were tested and compared with activity of BAP, which is known to be highly active cytokinin.

The compounds to be tested were dissolved in dimethylsulfoxide (DMSO) and the solution brought up to $10^{-3}$M with distilled water. This stock solution was further diluted with the respective media used for the biotest to a concentration ranging from $10^{-8}$ M to $10^{-4}$ M. The final concentration of DMSO did not exceed 0.2% and therefore did not affect the biological activity in the assay system used. The activity obtained for $10^{-4}$ M of BAP was postulated as 100%.

Newly developed compounds possess very strong antisenescent properties. Some of them cause 200% increase of chlorophyll content in detached wheat leaves in comparison to BAP.

TABLE 3

The effect of novel compounds on delaying senescence in detached leaf segments of Triticum aestivum cv. Hereward. The results are expressed in % of initial content of chlorophyll in fresh leaves before incubation.

| Compound | maximum effective concentration (mol · l$^{-1}$) | activity (%) [$10^{-4}$ mol · l$^{-1}$ BAP = 100%] |
|---|---|---|
| 6-furfurylamino-9-β-D-arabinofuranosylpurine | $10^{-4}$ | 193 ± 1 |
| 6-(3-methoxybenzylamino)-9-β-D-arabinofuranosylpurine | $10^{-4}$ | 118 ± 2 |

TABLE 3-continued

The effect of novel compounds on delaying senescence in detached leaf segments of *Triticum aestivum* cv. Hereward. The results are expressed in % of initial content of chlorophyll in fresh leaves before incubation.

| Compound | maximum effective concentration (mol · l$^{-1}$) | activity (%) [10$^{-4}$ mol · l$^{-1}$ BAP = 100%] |
|---|---|---|
| 6-benzylaminopurine-9 β-D-deoxyribosylpurine | 10$^{-4}$ | 178 ± 9 |
| 6-(3-chlorobenzylamino)-9-β-D-arabinofuranosylpurine | 10$^{-4}$ | 172 ± 8 |
| 6-(3-fluorobenzylamino)-9-β-D-arabinofuranosylpurine | 10$^{-4}$ | 195 ± 6 |
| 6-(2-bromobenzylamino)-9-β-D-arabinofuranosylpurine | 10$^{-5}$ | 186 ± 19 |
| 6-(3-bromobenzylamino)-9-β-D-arabinofuranosylpurine | 10$^{-4}$ | 198 ± 10 |
| 6-(4-bromobenzylamino)-9-β-D-arabinofuranosylpurine | 10$^{-4}$ | 176 ± 11 |
| 6-(3-iodobenzylamino)-9-β-D-arabinofuranosylpurine | 10$^{-4}$ | 198 ± 4 |
| 6-(3,4-dimethoxybenzylamino)-9-β-D-arabinofuranosylpurine | 10$^{-4}$ | 147 ± 6 |
| 6-(3-chlorobenzylamino)-9-riboside (comparative example) | 10$^{-4}$ | 72 ± 8 |
| 6-(3-iodobenzylamino)-9-riboside (comparative example) | 10$^{-4}$ | 58 ± 19 |
| 6-(3-bromobenzylamino)-9-riboside (comparative example) | 10$^{-4}$ | 89 ± 10 |
| 6-(3,4-dimethoxybenzylamino)-9-riboside (comparative example) | 10$^{-4}$ | 47 ± 6 |
| 6-(2,4-dichlorbenzylamino)-9-riboside (comparative example) | 10$^{-4}$ | 5 ± 1 |

Example 16: Controlling Shoot-Tip Necrosis in Shoot Cultures of *Dais cotinifolia*—an Ornamental Flowering Tree Young shoot-tip (approximately, 10 mm) explants of *Dais cotinifolia* were collected from the Botanical Garden, University of KwaZulu-Natal, Pietermaritzburg, South Africa. Explants were washed thoroughly with 0.1% (v/v) of Tween® 20 for 2 min, and decontaminated with 70% ethanol for 15 sec followed by 0.2% aqueous HgCl$_2$ for 10 min. The explants were rinsed five times with sterile distilled water. Disinfected explants (approximately, 5 mm) were cultured in MS (Murashige and Skoog 1962) medium containing 30 g L$^{-1}$ sucrose, 8 g L$^{-1}$ agar and 5 μM benzyladenine (BA) for in vitro shoot cultures. Shoot tips (approximately, 0.5 cm) of *Dais cotinifolia* were collected from two-month-old in vitro shoot cultures and were cultured in MS medium containing 30 g L$^{-1}$ sucrose, 8 g L$^{-1}$ agar and 10 μM BA or different concentrations of chemical compounds (5, 10, 20 and 30 μM 3CH3BAPA or 2FBAPA; 2FBAPA=6-(2-fluorobenzylamino)-9-β-D-arabinofuranosylpurine; 3CH3BAPA=6-(3-methylbenzylamino)-9-β-D-arabinofuranosylpurine) for adventitious shoot regeneration and evaluation of shoot-tip necrosis (STN) for 8 weeks. The precise concentration of compounds of shoot-tip cultures are indicated in Table 1. Medium lacking plant growth regulators served as a control. The chemicals used were of analytical grade (Biolab, South Africa; Oxoid, England and Sigma, USA). All media were adjusted to pH 5.8 with 0.1 N NaOH before gelling with 8 g L$^{-1}$ agar and autoclaving at 121° C. for 20 min. The cultures were maintained under 16 h photoperiod supplied by cool white fluorescent light [40 μmol m$^{-2}$ s$^{-1}$ photosynthetic photon flux (PPF), OSRAM L 58 W/740, South Africa] at 25±2° C. Data were subjected to one-way analysis of variance (ANOVA) using SPSS version 22.0 for Windows (Chicago, Ill., USA). Significantly different means were separated using Duncan's multiple range test (P=0.05). Each value was presented as the mean±standard error, with three replicates; each replicate consisting of 15 explants per treatment.

Effect of BA, 3CH3BAPA and 2FBAPA on shoot multiplication and shoot-tip necrosis from shoot-tip explants of *Dais cotinifolia* (STN=Shoot-tip necrosis. SBI=Shoot bud initiation. The data were recorded after 8 weeks of culture. Values are mean±standard error (SE) from three replicates per treatment. Means followed by same letters in each column are not significantly different (P=0.05) using Duncan's multiple range test):

| Plant growth regulators [μM] in MS medium | Shoots [explant$^{-1}$] [#] | Shoot length [cm] | STN [%] | Morphogenesis in vitro |
|---|---|---|---|---|
| control | 1.0 ± 0.00c | 2.00 ± 0.35ab | 50.0 ± 1.09bc | Pale green shoots |
| 10 BA | 3.4 ± 0.37a | 1.52 ± 0.26bc | 61.5 ± 1.02a | Dark green shoots + SBI |
| 5 3CH3BAPA | 1.0 ± 0.00c | 1.42 ± 0.21bc | 52.2 ± 0.89b | Green shoots |
| 10 3CH3BAPA | 1.0 ± 0.00c | 1.86 ± 0.14ab | 50.0 ± 0.75bc | Green shoots |
| 20 3CH3BAPA | 1.8 ± 0.48bc | 1.94 ± 0.09ab | 45.5 ± 0.95d | Pale green shoots |
| 30 3CH3BAPA | 2.2 ± 0.32b | 2.26 ± 0.22a | 31.3 ± 1.12ef | Pale green shoots |
| 5 2FBAPA | 1.0 ± 0.00c | 1.12 ± 0.12bc | 33.3 ± 0.74e | Pale green shoots |

-continued

| Plant growth regulators [μM] in MS medium | Shoots [explant$^{-1}$] [#] | Shoot length [cm] | STN [%] | Morphogenesis in vitro |
|---|---|---|---|---|
| 10 2FBAPA | 1.6 ± 0.24bc | 1.54 ± 0.16bc | 31.5 ± 1.18ef | Pale green shoots |
| 20 2FBAPA | 2.0 ± 0.32b | 1.90 ± 0.14ab | 27.7 ± 0.74g | Green shoots |
| 30 2FBAPA | 2.3 ± 0.37b | 2.40 ± 0.27a | 20.0 ± 0.44h | Green shoots |

Example 17: Micropropagation of *Harpagophytum procumbens* and *Amelanchier alnifolia* Using 3CH$_3$BAPA and 2FBAPA (2FBAPA=6-(2-fluorobenzylamino)-9-β-D-arabinofuranosylpurine; 3CH3BAPA=6-(3-methylbenzylamino)-9-β-D-arabinofuranosylpurine)

Experimental Design

Previously initiated cultures of *Harpagophytum procumbens* were used as the source of nodal explants. The cultured was initiated from materially collected in the wild which was positively identified at the Bews Herbarium, University of KwaZulu-Natal, Pietermaritzburg, South Africa. The Stock cultures were regularly sub-cultured to fresh medium every 3-4 weeks and incubated in a growth room with cool fluorescent tubes (Osram L75W/20X) at a light intensity of 45 μmol m$^{-2}$ s–1 and a temperature of 25±1° C. in a 16 h photoperiod. *Amelanchier alnifolia* was obtained as sterile culture from a commercial company (Czech Republic). Cultures of *Harpagophytum procumbens* were maintained on 5 μM BAP while *Amelanchier alnifolia* was maintained on 1 mg/ml meta-topolin. For the current study, the effect of BAP with either 3CH$_3$BAPA or 2FBAPA on shoot proliferation in *Harpagophytum procumbens* and *Amelanchier alnifolia* were conducted using sterile culture of these aforementioned species. The nodal section (measuring approximately 1×1 cm$^2$ were used as explant type for both species.

In order to investigate the biological effect of 3CH$_3$BAPA and 2FBAPA, both compounds were tested at four (5; 10; 20 and 30 μM) concentrations with 10 μM BAP. The cultures were incubated in 16/8 h light/dark conditions with a photosynthetic photon flux density (PPFD) of 45 μmol m$^{-2}$ s$^{-1}$ at 25±2° C. After 35 days, shoot number, shoot length and fresh weight were measured and recorded. The parameters of the treatment and the results are summarized in the following tables and in FIG. 5.

| Treatment No. | BAP (μM) | Compound (μM) | |
|---|---|---|---|
| 1 | 0 | 0 | |
| 2 | 10 | 0 | |
| 3 | 10 | 5 | 3CH3BAPA |
| 4 | 10 | 10 | |
| 5 | 10 | 20 | |
| 6 | 10 | 30 | |
| 7 | 10 | 5 | 2FBAPA |
| 8 | 10 | 10 | |
| 9 | 10 | 20 | |
| 10 | 10 | 30 | |

TABLE 4

Effect of the new compounds with BAP on growth response in *Harpagophytum procumbens* after 35 days in vitro. N = 12

| Treatment No. | Shoot no. mean SE | Shoot length (mm) mean SE | Fresh weight (g) mean SE |
|---|---|---|---|
| 1 | 1.6 ± 0.163 | 19.3 ± 2.85599 | 0.1966 ± 0.02902 |
| 2 | 1.5 ± 0.167 | 19.4 ± 1.52898 | 0.3614 ± 0.05563 |
| 3 | 2.8 ± 0.573 | 28.6 ± 4.39747 | 0.8607 ± 0.18838 |
| 4 | 2.6 ± 0.340 | 45.8 ± 7.09429 | 1.0523 ± 0.24387 |
| 5 | 2.3 ± 0.423 | 27 ± 3.53082 | 0.8456 ± 0.13386 |
| 6 | 3.8 ± 0.593 | 40.6 ± 4.83092 | 1.1419 ± 0.21301 |
| 7 | 1.7 ± 0.335 | 19.8 ± 3.2721 | 0.8764 ± 0.18181 |
| 8 | 2.5 ± 0.477 | 23.9 ± 3.19531 | 0.6712 ± 0.11492 |
| 9 | 2.8 ± 0.291 | 34.9 ± 5.60843 | 0.8935 ± 0.23103 |
| 10 | 2.4 ± 0.267 | 23.7 ± 2.93655 | 0.6877 ± 0.10093 |

TABLE 5

Effect of the new compounds with BAP on growth response in *Amelanchier alnifolia* after 35 days in vitro. N = 9

| Treatment No. | Shoot no. mean SE | Shoot length (mm) mean SE | Fresh weight (g) mean SE |
|---|---|---|---|
| 1 | 1.0 ± 0.00 | 18.56 ± 1.651 | 0.043 ± 0.0057 |
| 2 | 7.7 ± 2.65 | 17.22 ± 1.770 | 0.319 ± 0.1255 |
| 3 | 7.6 ± 2.10 | 14.11 ± 1.670 | 0.249 ± 0.0594 |
| 4 | 10.6 ± 2.75 | 18.89 ± 2.288 | 0.349 ± 0.1025 |
| 5 | 13.7 ± 2.06 | 16.22 ± 1.730 | 0.563 ± 0.0729 |
| 6 | 11.6 ± 2.99 | 18.33 ± 3.122 | 0.335 ± 0.0877 |
| 7 | 7.2 ± 1.41 | 14.33 ± 2.754 | 0.178 ± 0.0428 |
| 8 | 13.2 ± 3.44 | 14.67 ± 1.291 | 0.529 ± 0.1739 |
| 9 | 15.4 ± 1.62 | 19.33 ± 2.571 | 0.492 ± 0.0593 |
| 10 | 14.9 ± 2.40 | 16.44 ± 2.369 | 0.584 ± 0.1564 |

Example 18: Controlling Shoot-Tip Necrosis in In Vitro Cultures of *Gymnosporia buxfolia*—A Medicinal Plant Mature seeds of *Gymnosporia buxfolia* were collected from the Botanical garden, University of KwaZulu-Natal, Pietermaritzburg, South Africa. Seeds were washed thoroughly with 0.2% (v/v) of Tween® 20 for 5 min, and decontaminated with 0.2% aqueous HgCl$_2$ for 12 min. The seeds were then rinsed five times with sterile distilled water. Decontaminated seeds were inoculated onto MS (Murashige and Skoog 1962) medium containing 30 g L$^{-1}$ sucrose and 8 g L$^{-1}$ agar for in vitro germination. Shoot-tip explants (approximately, 10 mm) of 20-day-old in vitro seedlings were cultured in MS medium supplemented with 10 μM BA (6-benzylaminopurine) and 5, 10, 20 and 30 μM 3CH3BAPA or 2FBAPA (2FBAPA=6-(2-fluorobenzylamino)-9-β-D-arabinofuranosylpurine; 3CH3BAPA=6-(3-methylbenzylamino)-9-β-D-arabinofuranosylpurine) respectively for shoot multiplication and evaluation of shoot-tip necrosis (STN). The precise concentration of compounds of shoot-tip cultures are indicated in Table 1. Medium lacking plant growth regulators served as a control.

The chemicals used were of analytical grade (Biolab, South Africa; Oxoid, England and Sigma, USA). All media were adjusted to pH 5.8 with 0.1 N NaOH before gelling with 8 g $L^{-1}$ agar and autoclaving at 121° C. for 20 min. The cultures were maintained under 16 h photoperiod supplied by cool white fluorescent light [40 μmol $m^{-2}$ $s^{-1}$ photosynthetic photon flux (PPF), OSRAM L 58 W/740, South Africa] at 25±2° C. Data were collected after 4 weeks of culture. All experiments were done triplicate with 12 explants per treatment. Data were subjected to one-way analysis of variance (ANOVA) using SPSS version 22.0 for Windows (Chicago, Ill., USA). Significantly different means were separated using Duncan's multiple range test (P=0.05).

Effect of BA, 3CH3BAPA and 2FBAPA on shoot-tip necrosis from shoot-tip explants of *Gymnosporia buxifolia* (STN=Shoot-tip necrosis. The data were recorded after 4 weeks of culture. Values are mean±standard error (SE) from three replicates per treatment. Means followed by same letters in each column are not significantly different (P=0.05) using Duncan's multiple range test):

| Plant growth regulators [μM] in MS medium | Shoots [explant$^{-1}$] [#] | Shoot length [cm] | STN [%] |
|---|---|---|---|
| control | 1.0 ± 0.0a | 1.90 ± 0.33b | 46.7 ± 0.51e |
| 10 BA | 1.0 ± 0.0a | 1.92 ± 0.09b | 73.3 ± 0.20a |
| 5 3CH3BAPA | 1.0 ± 0.0a | 1.36 ± 0.27bc | 53.3 ± 0.24d |
| 10 3CH3BAPA | 1.0 ± 0.0a | 1.82 ± 0.17b | 40.0 ± 0.20fg |
| 20 3CH3BAPA | 1.0 ± 0.0a | 3.30 ± 0.14a | 22.6 ± 0.28hi |
| 30 3CH3BAPA | 1.0 ± 0.0a | 3.00 ± 0.11a | 13.3 ± 0.24j |
| 5 2FBAPA | 1.0 ± 0.0a | 1.02 ± 0.15bc | 66.7 ± 0.32b |
| 10 2FBAPA | 1.0 ± 0.0a | 1.82 ± 0.13b | 58.0 ± 0.40c |
| 20 2FBAPA | 1.0 ± 0.0a | 3.20 ± 0.17a | 42.0 ± 1.20f |
| 30 2FBAPA | 1.0 ± 0.0a | 2.98 ± 0.12a | 26.6 ± 0.37h |

Example 19: Differential Gene Expression Study

Comparative gene expression analysis in *Arabidopsis* model was performed to gain information about the reprogramming of gene transcription when senescent leaves were treated with 6-(3-methoxybenzylamino)-9-β-D-arabinofuranosylpurine (3MeOBAPA).

For isolation of total RNA, *Arabidopsis* wild-type plants (Col-0) were used, which were either treated with 3MeOBAPA or left untreated. Wild-type plants were grown in soil for 30 days, and then leaves of similar size and chlorophyll content were cut and immediately used for the treatment. At least 20 detached leaves were submerged in 1×MS medium supplemented with 10 μM 3MeOBAPA. Control samples were mock treated with DMSO only. After incubation for 6 h or 48 h in the dark, detached leaves were frozen in liquid nitrogen and used for RNA isolation; 150 mg of liquid nitrogen-ground material was used per isolation. cDNA sequencing libraries were prepared with the Illumina TruSeq Stranded mRNA LT Sample Prep Kit (Illumina, San Diego, Calif.) according to standard Illumina's protocols and sequenced on HiSeq 2500 apparatus (50 bp single-end reads).

Data were subjected to differential transcriptomic analysis with the aim to reveal significantly regulated genes and their expression levels. To gain insight into the molecular mechanism of 3MeOBAPA action in *Arabidopsis* we decided to analyze the gene expression patterns via comparison of mock (DMSO)-treated plants with those obtained after i) short time treatment with 3MeOBAPA (6 h) and ii) long time treatment (48 h). This comparison leads to identification of group of genes with similar kinetic of expression and helps to understand possible mechanism of regulation. For data analysis, we performed ab initio method where sequencing reads were mapped to the reference genome. The short time treatment resulted in reprogramming of the gene transcription compared to the mock-treated control with 1119 downregulated and 1102 upregulated genes (P≤0.05). Further treatment with 3MeOBAPA (i.e. 48 h) led to alterations in the expression profiles and, thus, we could observe more profound changes in the numbers of affected genes: 7 095 genes were downregulated and 7509 genes were upregulated (P≤0.05). Analysis of regulated genes in both groups (short time treatment vs. long time treatment) showed a substantial overlap in the two categories. Indeed, we could detect 1102 genes that were upregulated in response to 3MeOBAPA treatment and 724 genes that were downregulated in both groups (FIG. 7). The overlap is particularly visible in the group of upregulated genes suggesting a rapid response to the elicitation after 6 h treatment that reaches maximal values after 48 h incubation with 3MeOBAPA. This trend is well documented in the list of top 50 genes upregulated in response to 3MeOBAP treatment (Tab. 6). As evident, all genes that were upregulated after 6 h of the treatment probably remain activated over a period of 48 h and their expression levels in the latter time point are one or two orders of magnitude higher than those recorded in 6 h.

A closer inspection of the top 50 3MeOBAPA upregulated genes reveals that several most abundant gene transcripts present in both groups are related directly to plant defense mechanisms (Tab. 6). This was the case of plant defensins family proteins including At5g44430 coding for defensin-like protein 1.2C, At5g44420 coding for defensin-like protein 1.2A, At2g26020 coding for defensin-like protein 1.2B or At2g26010 coding for defensin-like protein 1.3 which are important anti-stress factors upregulated in response to pathogen or stress elicitation and, importantly, also during plant senescence. Moreover, we also detected high expression levels of several enzymes involved in modifications and in remodeling of cell wall that are also important for pollen tube growth. These enzymes belong either to pectin methylesterase or pectin lyase families, such as At2g47040 coding for pectin methylesterase Vanguard1 and At3g07820 coding for pectin lyase-like superfamily protein, or, interestingly, there were also genes coding for enzymes with combined pectin methylesterase/pectin methylesterase inhibitor activity such as At2g47050 or At3g05610. Other enzymes of cell wall synthesis were also detected such as products of gene At4g35010 coding for β-galactosidase 11 (BGAL11), At1g02790 coding for polygalacturonase 4 (PGA4) or At3g62710 coding for glycosyl hydrolase family protein. This strongly suggests that in plants 3MeOBAP specifically regulates processes that are necessary for cell wall remodeling and consequent enhanced resistance to stresses and fungal pathogens.

TABLE 6

Top 50 genes upregulated in response to 3MeOBAPA treatment in two selected time points. Genes with P ≤ 0.05 that are changed both after 6 h and after 48 h of treatment with 10 μM 3MeOBAP are shown.

| AGI code | Description | logFC 6 h | logFC 48 h |
|---|---|---|---|
| AT2G47040 | Pectin methylesterase Vanguard1 (VGD1) | 2.80 | 5.89 |
| AT2G47050 | Plant invertase/pectin methylesterase inhibitor superfamily protein | 2.31 | 5.82 |
| AT3G07820 | Pectin lyase-like superfamily protein | 2.22 | 6.45 |
| AT4G35010 | Beta-galactosidase 11 (BGAL11) | 2.03 | 5.33 |
| AT3G05610 | Pectinesterase/pectinesterase inhibitor 21 (PME21) | 1.80 | 5.58 |
| AT5G44430 | Defensin-like protein 1.2C (PDF1.2C) | 1.75 | 8.87 |
| AT1G55560 | SKU5 similar 14 (SKS14) | 1.71 | 8.75 |
| AT1G02790 | Polygalacturonase 4 (PGA4) | 1.67 | 8.59 |
| AT5G44420 | Defensin-like protein 1.2A (PDF1.2A) | 1.58 | 8.15 |
| AT2G26020 | Defensin-like protein 1.2B (PDF1.2B) | 1.52 | 6.04 |
| AT2G26010 | Defensin-like protein 1.3 (PDF1.3) | 1.47 | 8.23 |
| AT5G45880 | Pollen Ole e 1 allergen and extensin family protein | 1.45 | 5.52 |
| AT3G62710 | Glycosyl hydrolase family protein | 1.35 | 5.26 |
| AT5G12960 | Putative glycosyl hydrolase | 1.33 | 5.26 |
| AT1G05580 | Cation/H(+) exchanger 23 (CHX23) | 1.26 | 5.46 |
| AT2G04460 | Transposable element gene | 1.16 | 5.43 |
| AT5G61160 | Agmatine coumaroyltransferase (ACT) | 1.13 | 5.05 |
| AT1G59950 | NAD(P)-linked oxidoreductase superfamily protein | 1.08 | 5.72 |
| AT1G75830 | Defensin-like protein 1.1 (PDF1.1) | 1.06 | 7.85 |
| AT3G28153 | Transposable element gene | 0.92 | 5.70 |
| AT2G28210 | Alpha carbonic anhydrase 2 (ATACA2) | 0.85 | 5.86 |
| AT3G13400 | SKU5 similar 13 (SKS13) | 0.82 | 5.57 |
| AT4G01390 | TRAF-like family protein | 0.79 | 6.24 |
| AT1G76640 | Calcium-binding EF-hand family protein (CML39) | 0.78 | 7.06 |
| AT2G18150 | Peroxidase 15 (PER15) | 0.68 | 7.22 |
| AT4G24350 | Phosphorylase superfamily protein | 0.64 | 6.45 |
| AT1G19670 | Chlorophyllase-1 (CLH1) | 0.63 | 6.42 |
| AT3G28155 | ARM repeat superfamily protein | 0.59 | 6.06 |
| AT1G15540 | 2-oxoglutarate and Fe(II)-dependent oxygenase superfamily protein | 0.57 | 5.63 |
| AT5G52670 | Copper transport family protein | 0.57 | 6.03 |
| AT5G63270 | RPM1-interacting protein 4 (RIN4) family protein | 0.56 | 7.11 |
| AT2G39030 | L-ornithine N5-acetyltransferase (NATA1) | 0.56 | 5.48 |
| AT4G21830 | Peptide methionine sulfoxide reductase B7 (MSRB7) | 0.55 | 5.95 |
| AT3G09340 | Transmembrane amino acid transporter family protein | 0.55 | 8.54 |
| AT2G02010 | Glutamate decarboxylase 4 (GAD4) | 0.55 | 5.09 |
| AT2G21900 | WRKY transcription factor 59 (WRKY59) | 0.54 | 5.81 |
| AT4G26010 | Peroxidase 44 (PER44) | 0.53 | 7.92 |
| AT3G11340 | UDP-Glycosyltransferase superfamily protein | 0.51 | 6.60 |
| AT2G26695 | Ran BP2/NZF zinc finger-like superfamily protein | 0.50 | 5.90 |
| AT1G59860 | 17.6 kDa class I heat shock protein 1 (HSP17.6A) | 0.48 | 5.47 |
| AT4G22620 | SAUR-like auxin-responsive family protein | 0.46 | 5.05 |
| AT4G39320 | Microtubule-associated protein-related | 0.45 | 5.09 |
| AT5G62720 | Integral membrane HPP family protein | 0.44 | 5.31 |
| AT2G37430 | Zinc finger protein ZAT11 | 0.42 | 4.96 |
| AT5G03610 | GDSL esterase/lipase | 0.42 | 4.61 |
| AT4G37780 | Myb domain protein 87 (MYB87) | 0.41 | 6.88 |
| AT4G22030 | F-box domain, cyclin-like, F-box domain, Skp2-like protein | 0.41 | 5.02 |
| AT1G10585 | Basic helix-loop-helix (bHLH) DNA-binding superfamily protein | 0.38 | 4.85 |
| AT3G44830 | Putative phospholipid:diacylglycerol acyltransferase 2 (PDAT2) | 0.38 | 4.91 |
| AT4G31950 | Cytochrome P450 82C3 (CYP82C3) | 0.37 | 5.29 |

The invention claimed is:

1. A method for regulation of aging in plants in vivo or plant cells in vitro, and for regulation of growth and development of plants in vivo, plant tissues, plant organs and plant cells in vitro, in which at least one compound of general formula I is applied to the said plant, plant tissues, plant organs or plant cells, wherein the compound of general formula I is

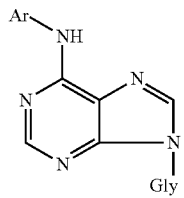

or pharmaceutically acceptable salts thereof with alkali metals, ammonia, amines, or addition salts with acids, wherein Gly represents β-D-arabinofuranosyl or β-D-2'-deoxyribofuranosyl, Ar represents benzyl or furfuryl, each of which can be unsubstituted or substituted by one or more substituents selected from the group consisting of hydroxyl, alkyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, and trifluoromethoxy.

2. The method according to claim 1, wherein the compound of general formula I is selected from the group consisting of:

6-furfurylamino-9-β-D-arabinofuranosylpurine,
6-(3-methylfurfurylamino)-9-β-D-arabinofuranosylpurine,
6-(4-methylfurfurylamino)-9-β-D-arabinofuranosylpurine,
6-(5-methylfurfurylamino)-9-β-D-arabinofuranosylpurine,
6-(3-fluorofurfurylamino)-9-β-D-arabinofuranosylpurine,
6-(4-fluorofurfurylamino)-9-β-D-arabinofuranosylpurine,
6-(5-fluorofurfurylamino)-9-β-D-arabinofuranosylpurine,
6-(3-chlorofurfurylamino)-9-β-D-arabinofuranosylpurine,
6-(4-chorofurfurylamino)-9-β-D-arabinofuranosylpurine,
6-(5-chlorofurfurylamino)-9-β-D-arabinofuranosylpurine,
6-(3-bromofurfurylamino)-9-β-D-arabinofuranosylpurine,
6-(4-bromofurfurylamino)-9-β-D-arabinofuranosylpurine,
6-(5-bromofurfurylamino)-9-β-D-arabinofuranosylpurine,
6-(3-hydroxyfurfurylamino)-9-β-D-arabinofuranosylpurine,
6-(4-hydroxyfurfurylamino)-9-β-D-arabinofuranosylpurine,
6-(5-hydroxyfurfurylamino)-9-β-D-arabinofuranosylpurine,
6-(3-methoxyfurfurylamino)-9-β-D-arabinofuranosylpurine,
6-(4-methoxyfurfurylamino)-9-β-D-arabinofuranosylpurine,
6-(5-methoxyfurfurylamino)-9-β-D-arabinofuranosylpurine,
6-(2-aminofurfurylamino)-9-β-D-arabinofuranosylpurine,
6-(3-aminofurfurylamino)-9-β-D-arabinofuranosylpurine,
6-(4-aminofurfurylamino)-9-β-D-arabinofuranosylpurine,
6-(3,4-dihydroxyfurfurylamino)-9-β-D-arabinofuranosylpurine,
6-(3,5-dihydroxyfurfurylamino)-9-β-D-arabinofuranosylpurine,
6-(3,4-dihydroxyfurfurylamino)-9-β-D-arabinofuranosylpurine,
6-(2,4-dihydroxyfurfurylamino)-9-β-D-arabinofuranosylpurine,
6-(2,5-dihydroxyfurfurylamino)-9-β-D-arabinofuranosylpurine,
6-(2,6-dihydroxyfurfurylamino)-9-β-D-arabinofuranosylpurine,
6-(3,4-dimethoxyfurfurylamino)-9-β-D-arabinofuranosylpurine,
6-(3,4-dimethoxyfurfurylamino)-9-β-D-arabinofuranosylpurine,
6-(3,5-dimethoxyfurfurylamino)-9-β-D-arabinofuranosylpurine,
6-(2,3-dimethoxyfurfurylamino)-9-β-D-arabinofuranosylpurine,
6-(2,4-dimethoxyfurfurylamino)-9-β-D-arabinofuranosylpurine,
6-(2,5-dimethoxyfurfurylamino)-9-β-D-arabinofuranosylpurine,
6-(2,6-dimethoxyfurfurylamino)-9-β-D-arabinofuranosylpurine,
6-(2-hydroxy-3-methoxyfurfurylamino)-9-β-D-arabinofuranosylpurine,
6-(2-hydroxy-4-methoxyfurfurylamino)-9-β-D-arabinofuranosylpurine,
6-(2-hydroxy-5-methoxyfurfurylamino)-9-β-D-arabinofuranosylpurine,
6-(2-hydroxy-6-methoxyfurfurylamino)-9-β-D-arabinofuranosylpurine,
6-(3-hydroxy-2-methoxyfurfurylamino)-9-β-D-arabinofuranosylpurine,
6-(3-hydroxy-4-methoxyfurfurylamino)-9-β-D-arabinofuranosylpurine,
6-(3-hydroxy-5-methoxyfurfurylamino)-9-β-D-arabinofuranosylpurine,
6-(3-hydroxy-6-methoxyfurfurylamino)-9-β-D-arabinofuranosylpurine,
6-(4-hydroxy-2-methoxyfurfurylamino)-9-β-D-arabinofuranosylpurine,
6-(4-hydroxy-3-methoxyfurfurylamino)-9-β-D-arabinofuranosylpurine,
6-(4-hydroxy-5-methoxyfurfurylamino)-9-β-D-arabinofuranosylpurine,
6-(4-hydroxy-6-methoxyfurfurylamino)-9-β-D-arabinofuranosylpurine,
6-(2-fluorobenzylamino)-9-β-D-arabinofuranosylpurine,
6-(3-fluorobenzylamino)-9-β-D-arabinofuranosylpurine,
6-(4-fluorobenzylamino)-9-β-D-arabinofuranosylpurine,
6-(2-bromobenzylamino)-9-β-D-arabinofuranosylpurine,
6-(3-bromobenzylamino)-9-β-D-arabinofuranosylpurine,
6-(4-bromobenzylamino)-9-β-D-arabinofuranosylpurine,
6-(2-iodobenzylamino)-9-β-D-arabinofuranosylpurine,
6-(3-iodobenzylamino)-9-β-D-arabinofuranosylpurine,
6-(4-iodobenzylamino)-9-β-D-arabinofuranosylpurine, 6-(2-chlorobenzylamino)-9-β-D-arabinofuranosylpurine,
6-(2-chlorobenzylamino)-9-β-D-arabinofuranosylpurine,
6-(3-chlorobenzylamino)-9-β-D-arabinofuranosylpurine,
6-(4-chlorobenzylamino)-9-β-D-arabinofuranosylpurine,
6-(2-methoxybenzylamino)-9-β-D-arabinofuranosylpurine,
6-(3-methoxybenzylamino)-9-β-D-arabinofuranosylpurine,
6-(4-methoxybenzylamino)-9-β-D-arabinofuranosylpurine,
6-(2-hydroxybenzylamino)-9-β-D-arabinofuranosylpurine,
6-(3-hydroxybenzylamino)-9-β-D-arabinofuranosylpurine,
6-(4-hydroxybenzylamino)-9-β-D-arabinofuranosylpurine,
6-(4-hexylbenzylamino)-9-β-D-arabinofuranosylpurine,
6-(2-fluoro-6-(trifluoromethyl)benzylamino)-9-β-D-arabinofuranosylpurine,
6-(3-chloro-2,6-difluorobenzylamino)-9-β-D-arabinofuranosylpurine,
6-(3-(trifluoromethylthio)benzylamino)-9-β-D-arabinofuranosylpurine,
6-(2-chloro-3,6-difluorobenzylamino)-9-β-D-arabinofuranosylpurine,
6-(4-(trifluoromethylthio)benzylamino)-9-β-D-arabinofuranosylpurine,
6-(3-fluoro-5-(trifluoromethyl)benzylamino)-9-β-D-arabinofuranosylpurine,
6-(2-chloro-4-fluorobenzylamino)-9-β-D-arabinofuranosylpurine,
6-(2-(trifluoromethoxy)benzylamino)-9-β-D-arabinofuranosylpurine,
6-(3-(trifluoromethyl)benzylamino)-9-β-D-arabinofuranosylpurine,
6-(2-(trifluoromethyl)benzylamino)-9-β-D-arabinofuranosylpurine,
6-(4-(trifluoromethyl)benzylamino)-9-β-D-arabinofuranosylpurine,
6-(4-chloro-3-(trifluoromethyl)benzylamino)-9-β-D-arabinofuranosylpurine,
6-(4-fluoro-3-(trifluoromethyl)benzylamino)-9-β-D-arabinofuranosylpurine,
6-(3,5-bis(trifluoromethyl)benzylamino)-9-β-D-arabinofuranosylpurine,
6-(3-(trifluoromethoxy)benzylamino)-9-β-D-arabinofuranosylpurine,
6-(4-(trifluoromethoxy)benzylamino)-9-β-D-arabinofuranosylpurine,
6-(4-(trifluoromethyl)benzylamino)-9-β-D-arabinofuranosylpurine,
6-(2-aminobenzylamino)-9-β-D-arabinofuranosylpurine,
6-(3-aminobenzylamino)-9-β-D-arabinofuranosylpurine,
6-(4-aminobenzylamino)-9-β-D-arabinofuranosylpurine,
6-(4-diethylaminobenzylamino)-9-β-D-arabinofuranosylpurine,
6-(3,4-dihydroxybenzylamino)-9-β-D-arabinofuranosylpurine,
6-(3,5-dihydroxybenzylamino)-9-β-D-arabinofuranosylpurine,
6-(3,4-dihydroxybenzylamino)-9-β-D-arabinofuranosylpurine,
6-(2,4-dihydroxybenzylamino)-9-β-D-arabinofuranosylpurine,
6-(2,5-dihydroxybenzylamino)-9-β-D-arabinofuranosylpurine,
6-(2,6-dihydroxybenzylamino)-9-β-D-arabinofuranosylpurine,
6-(3,4-dimethoxybenzylamino)-9-β-D-arabinofuranosylpurine,
6-(3,4-dimethoxybenzylamino)-9-β-D-arabinofuranosylpurine,
6-(3,5-dimethoxybenzylamino)-9-β-D-arabinofuranosylpurine,
6-(2,3-dimethoxybenzylamino)-9-β-D-arabinofuranosylpurine,
6-(2,4-dimethoxybenzylamino)-9-β-D-arabinofuranosylpurine,
6-(2,5-dimethoxybenzylamino)-9-β-D-arabinofuranosylpurine,
6-(2,6-dimethoxybenzylamino)-9-β-D-arabinofuranosylpurine,
6-(2-hydroxy-3-methoxybenzylamino)-9-β-D-arabinofuranosylpurine,
6-(2-hydroxy-4-methoxybenzylamino)-9-β-D-arabinofuranosylpurine,
6-(2-hydroxy-5-methoxybenzylamino)-9-β-D-arabinofuranosylpurine,
6-(2-hydroxy-6-methoxybenzylamino)-9-β-D-arabinofuranosylpurine,
6-(3-hydroxy-2-methoxybenzylamino)-9-β-D-arabinofuranosylpurine,
6-(3-hydroxy-4-methoxybenzylamino)-9-β-D-arabinofuranosylpurine,
6-(3-hydroxy-5-methoxybenzylamino)-9-β-D-arabinofuranosylpurine,
6-(3-hydroxy-6-methoxybenzylamino)-9-β-D-arabinofuranosylpurine,
6-(4-hydroxy-2-methoxybenzylamino)-9-β-D-arabinofuranosylpurine,
6-(4-hydroxy-3-methoxybenzylamino)-9-β-D-arabinofuranosylpurine,
6-(4-hydroxy-5-methoxybenzylamino)-9-β-D-arabinofuranosylpurine,
6-(4-hydroxy-6-methoxybenzylamino)-9-β-D-arabinofuranosylpurine,
6-(2,3,4-trimethoxybenzylamino)-9-β-D-arabinofuranosylpurine,
6-(2,4,5-trimethoxybenzylamino)-9-β-D-arabinofuranosylpurine,
6-(2,4,6-trimethoxybenzylamino)-9-β-D-arabinofuranosylpurine,
6-(3,4,5-trimethoxybenzylamino)-9-β-D-arabinofuranosylpurine,
6-(2-hydroxy-3,4,5-trimethoxybenzylamino)-9-β-D-arabinofuranosylpurine,
6-(2-hydroxy-3,4,6-trimethoxybenzylamino)-9-β-D-arabinofuranosylpurine,
6-(2-hydroxy-4,5,6-trimethoxybenzylamino)-9-β-D-arabinofuranosylpurine,
6-(2,4,6-trimethoxybenzylamino)-9-β-D-arabinofuranosylpurine,
6-(2,3,4-trihydroxybenzylamino)-9-β-D-arabinofuranosylpurine,
6-(2,4,6-trihydroxybenzylamino)-9-β-D-arabinofuranosylpurine,
6-(2,3,4-trihydroxybenzylamino)-9-β-D-arabinofuranosylpurine,
6-(3,4,5-trihydroxybenzylamino)-9-β-D-arabinofuranosylpurine,
6-(2,4,6-trihydroxybenzylamino)-9-β-D-arabinofuranosylpurine, 6-(2-hydroxy-3-chlorobenzylamino)-9-β-D-arabinofuranosylpurine,
6-(2-hydroxy-4-chlorobenzylamino)-9-β-D-arabinofuranosylpurine,
6-(2-hydroxy-5-chlorobenzylamino)-9-β-D-arabinofuranosylpurine,
6-(2-hydroxy-6-chlorobenzylamino)-9-β-D-arabinofuranosylpurine,
6-(2-hydroxy-3-iodobenzylamino)-9-β-D-arabinofuranosylpurine,
6-(2-hydroxy-4-iodobenzylamino)-9-β-D-arabinofuranosylpurine,
6-(2-hydroxy-5-iodobenzylamino)-9-β-D-arabinofuranosylpurine,
6-(2-hydroxy-6-iodobenzylamino)-9-β-D-arabinofuranosylpurine,
6-(2-hydroxy-3-bromobenzylamino)-9-β-D-arabinofuranosylpurine,
6-(2-hydroxy-4-bromobenzylamino)-9-β-D-arabinofuranosylpurine,
6-(2-hydroxy-5-bromobenzylamino)-9-β-D-arabinofuranosylpurine,
6-(2-hydroxy-6-bromobenzylamino)-9-β-D-arabinofuranosylpurine,
6-(2-hydroxy-3-fluorobenzylamino)-9-β-D-arabinofuranosylpurine,
6-(2-hydroxy-4-fluorobenzylamino)-9-β-D-arabinofuranosylpurine,
6-(2-hydroxy-5-fluorobenzylamino)-9-β-D-arabinofuranosylpurine,
6-(3-methylfurfurylamino)-9-β-D-2'-deoxyribofuranosylpurine,
6-(4-methylfurfurylamino)-9-β-D-2'-deoxyribofuranosylpurine, 6-(5-methylfurfurylamino)-9-β-D-2'-deoxyribofuranosylpurine,
6-(3-fluorofurfurylamino)-9-β-D-2'-deoxyribofuranosylpurine,
6-(4-fluorofurfurylamino)-9-β-D-2'-deoxyribofuranosylpurine,
6-(5-fluorofurfurylamino)-9-β-D-2'-deoxyribofuranosylpurine,
6-(3-chlorofurfurylamino)-9-β-D-2'-deoxyribofuranosylpurine,
6-(4-chlorofurfurylamino)-9-β-D-2'-deoxyribofuranosylpurine,
6-(5-chlorofurfurylamino)-9-β-D-2'-deoxyribofuranosylpurine,
6-(3-bromo-furfurylamino)-9-β-D-2'-deoxyribofuranosylpurine,
6-(4-bromofurfurylamino)-9-β-D-2'-deoxyribofuranosylpurine,
6-(5-bromofurfurylamino)-9-β-D-2'-deoxyribofuranosylpurine,
6-(3-hydroxyfurfurylamino)-9-β-D-2'-deoxyribofuranosylpurine,
6-(4-hydroxyfurfurylamino)-9-β-D-2'-deoxyribofuranosylpurine,
6-(5-hydroxyfurfurylamino)-9-β-D-2'-deoxyribofuranosylpurine,
6-(3-methoxyfurfurylamino)-9-β-D-2'-deoxyribofuranosylpurine,
6-(4-methoxyfurfurylamino)-9-β-D-2'-deoxyribofuranosylpurine,
6-(5-methoxyfurfurylamino)-9-β-D-2'-deoxyribofuranosylpurine,
6-(2-aminofurfurylamino)-9-β-D-2'-deoxyribofuranosylpurine,
6-(3-aminofurfurylamino)-9-β-D-2'-deoxyribofuranosylpurine,
6-(4-aminofurfurylamino)-9-β-D-2'-deoxyribofuranosylpurine,
6-(3,4-dihydroxyfurfurylamino)-9-β-D-2'-deoxyribofuranosylpurine,
6-(3,5-dihydroxyfurfurylamino)-9-β-D-2'-deoxyribofuranosylpurine,
6-(3,4-dihydroxyfurfurylamino)-9-β-D-2'-deoxyribofuranosylpurine,
6-(2,4-dihydroxyfurfurylamino)-9-β-D-2'-deoxyribofuranosylpurine,
6-(2,5-dihydroxyfurfurylamino)-9-β-D-2'-deoxyribofuranosylpurine,
6-(2,6-dihydroxyfurfurylamino)-9-β-D-2'-deoxyribofuranosylpurine,
6-(3,4-dimethoxyfurfurylamino)-9-β-D-2'-deoxyribofuranosylpurine,
6-(3,4-dimethoxyfurfurylamino)-9-β-D-2'-deoxyribofuranosylpurine,
6-(3,5-dimethoxyfurfurylamino)-9-β-D-2'-deoxyribofuranosylpurine,
6-(2,3-dimethoxyfurfurylamino)-9-β-D-2'-deoxyribofuranosylpurine,
6-(2,4-dimethoxyfurfurylamino)-9-β-D-2'-deoxyribofuranosylpurine,
6-(2,5-dimethoxyfurfurylamino)-9-β-D-2'-deoxyribofuranosylpurine,
6-(2,6-dimethoxyfurfurylamino)-9-β-D-2'-deoxyribofuranosylpurine,
6-(2-hydroxy-3-methoxyfurfurylamino)-9-β-D-2'-deoxyribofuranosylpurine,
6-(2-hydroxy-4-methoxyfurfurylamino)-9-β-D-2'-deoxyribofuranosylpurine,
6-(2-hydroxy-5-methoxyfurfurylamino)-9-β-D-2'-deoxyribofuranosylpurine,
6-(2-hydroxy-6-methoxyfurfurylamino)-9-β-D-2'-deoxyribofuranosylpurine,
6-(3-hydroxy-2-methoxyfurfurylamino)-9-β-D-2'-deoxyribofuranosylpurine,
6-(3-hydroxy-4-methoxyfurfurylamino)-9-β-D-2'-deoxyribofuranosylpurine,
6-(3-hydroxy-5-methoxyfurfurylamino)-9-β-D-2'-deoxyribofuranosylpurine,
6-(3-hydroxy-6-methoxyfurfurylamino)-9-β-D-2'-deoxyribofuranosylpurine,
6-(4-hydroxy-2-methoxyfurfurylamino)-9-β-D-2'-deoxyribofuranosylpurine,
6-(4-hydroxy-3-methoxyfurfurylamino)-9-β-D-2'-deoxyribofuranosylpurine,
6-(4-hydroxy-5-methoxyfurfurylamino)-9-β-D-2'-deoxyribofuranosylpurine,
6-(4-hydroxy-6-methoxyfurfurylamino)-9-β-D-2'-deoxyribofuranosylpurine,
6-(2-fluorobenzylamino)-9-β-D-2'-deoxyribofuranosylpurine,
6-(3-fluorobenzylamino)-9-β-D-2'-deoxyribofuranosylpurine,
6-(4-fluorobenzylamino)-9-β-D-2'-deoxyribofuranosylpurine,
6-(2-bromobenzylamino)-9-β-D-2'-deoxyribofuranosylpurine,
6-(3-bromobenzylamino)-9-β-D-2'-deoxyribofuranosylpurine,
6-(4-bromobenzylamino)-9-β-D-2'-deoxyribofuranosylpurine, 6-(2-iodobenzylamino)-9-β-D-2'-deoxyribofuranosylpurine,
6-(3-iodobenzylamino)-9-β-D-2'-deoxyribofuranosylpurine,
6-(4-iodobenzylamino)-9-β-D-2'-deoxyribofuranosylpurine,
6-(2-chlorobenzylamino)-9-β-D-2'-deoxyribofuranosylpurine,
6-(2-chlorobenzylamino)-9-β-D-2'-deoxyribofuranosylpurine,
6-(3-chlorobenzylamino)-9-β-D-2'-deoxyribofuranosylpurine,
6-(4-chlorobenzylamino)-9-β-D-2'-deoxyribofuranosylpurine,
6-(2-aminobenzylamino)-9-β-D-2'-deoxyribofuranosylpurine,
6-(3-aminobenzylamino)-9-β-D-2'-deoxyribofuranosylpurine,
6-(4-aminobenzylamino)-9-β-D-2'-deoxyribofuranosylpurine,
6-(2-methoxybenzylamino)-9-β-D-2'-deoxyribofuranosylpurine,
6-(3-methoxybenzylamino)-9-β-D-2'-deoxyribofuranosylpurine,
6-(4-methoxybenzylamino)-9-β-D-2'-deoxyribofuranosylpurine, 6-(2-hydroxybenzylamino)-9-β-D-2'-deoxyribofuranosylpurine,
6-(3-hydroxybenzylamino)-9-β-D-2'-deoxyribofuranosylpurine,
6-(4-hydroxybenzylamino)-9-β-D-2'-deoxyribofuranosylpurine,
6-(3,4-dihydroxybenzylamino)-9-β-D-2'-deoxyribofuranosylpurine,
6-(3,5-dihydroxybenzylamino)-9-β-D-2'-deoxyribofuranosylpurine,
6-(3,4-dihydroxybenzylamino)-9-β-D-2'-deoxyribofuranosylpurine,
6-(2,4-dihydroxybenzylamino)-9-β-D-2'-deoxyribofuranosylpurine,
6-(2,5-dihydroxybenzylamino)-9-β-D-2'-deoxyribofuranosylpurine,
6-(2,6-dihydroxybenzylamino)-9-β-D-2'-deoxyribofuranosylpurine,
6-(3,4-dimethoxybenzylamino)-9-β-D-2'-deoxyribofuranosylpurine,
6-(3,4-dimethoxybenzylamino)-9-β-D-2'-deoxyribofuranosylpurine,
6-(3,5-dimethoxybenzylamino)-9-β-D-2'-deoxyribofuranosylpurine,
6-(2,3-dimethoxybenzylamino)-9-β-D-2'-deoxyribofuranosylpurine,
6-(2,4-dimethoxybenzylamino)-9-β-D-2'-deoxyribofuranosylpurine,
6-(2,5-dimethoxybenzylamino)-9-β-D-2'-deoxyribofuranosylpurine,
6-(2,6-dimethoxybenzylamino)-9-β-D-2'-deoxyribofuranosylpurine,
6-(2-hydroxy-3-methoxybenzylamino)-9-β-D-2'-deoxyribofuranosylpurine,
6-(2-hydroxy-4-methoxybenzylamino)-9-β-D-2'-deoxyribofuranosylpurine,
6-(2-hydroxy-5-methoxybenzylamino)-9-β-D-2'-deoxyribofuranosylpurine,
6-(2-hydroxy-6-methoxybenzylamino)-9-β-D-2'-deoxyribofuranosylpurine,
6-(3-hydroxy-2-methoxybenzylamino)-9-β-D-2'-deoxyribofuranosylpurine,
6-(3-hydroxy-4-methoxybenzylamino)-9-β-D-2'-deoxyribofuranosylpurine,
6-(3-hydroxy-5-methoxybenzylamino)-9-β-D-2'-deoxyribofuranosylpurine,
6-(3-hydroxy-6-methoxybenzylamino)-9-β-D-2'-deoxyribofuranosylpurine,
6-(4-hydroxy-2-methoxybenzylamino)-9-β-D-2'-deoxyribofuranosylpurine,
6-(4-hydroxy-3-methoxybenzylamino)-9-β-D-2'-deoxyribofuranosylpurine,
6-(4-hydroxy-5-methoxybenzylamino)-9-β-D-2'-deoxyribofuranosylpurine, and
6-(4-hydroxy-6-methoxybenzylamino)-9-β-D-2'-deoxyribofuranosylpurine.

3. The method according to claim 1, wherein the benzyl or furfuryl in Ar is substituted by one to three substituents selected from the group consisting of hydroxyl, alkyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, and trifluoromethoxy.

4. The method according to claim 1, wherein the regulation of aging in plants in vivo or plant cells in vitro is inhibition.

5. The method according to claim 1, wherein the regulation of development of plants and plant cells represents inhibiting, necrosis in plants and plant organs.

\* \* \* \* \*